(12) United States Patent
Lee et al.

(10) Patent No.: US 8,119,338 B2
(45) Date of Patent: Feb. 21, 2012

(54) METHODS AND COMPOSITIONS FOR DETECTING RHINOVIRUSES

(75) Inventors: Ming Chou Lee, Mission Viejo, CA (US); Lilly Kong, Covina, CA (US); Jan Groen, Laguna Niguel, CA (US)

(73) Assignee: Focus Diagnostics, Inc., Herndon, VA (US)

( * ) Notice: Subject to any disclaimer, the term of this patent is extended or adjusted under 35 U.S.C. 154(b) by 0 days.

(21) Appl. No.: 11/872,670

(22) Filed: Oct. 15, 2007

(65) Prior Publication Data

US 2008/0102444 A1    May 1, 2008

Related U.S. Application Data

(62) Division of application No. 10/886,517, filed on Jul. 6, 2004.

(51) Int. Cl.
*C12Q 1/70* (2006.01)
(52) U.S. Cl. .......................................... 435/5
(58) Field of Classification Search .................. None
See application file for complete search history.

(56) References Cited

U.S. PATENT DOCUMENTS

| | | | |
|---|---|---|---|
| 5,340,713 A * | 8/1994 | Torgersen et al. | 435/5 |
| 6,531,136 B1 | 3/2003 | Studdert et al. | |
| 2002/0142294 A1 | 10/2002 | Blair et al. | |
| 2002/0177125 A1 | 11/2002 | Kamb et al. | |
| 2003/0194712 A1 | 10/2003 | Lu et al. | |
| 2003/0203357 A1 | 10/2003 | Huang | |
| 2007/0134763 A1 | 6/2007 | Davies et al. | |

FOREIGN PATENT DOCUMENTS

| | | |
|---|---|---|
| EP | 00169146 | 1/1986 |
| EP | 00287395 | 10/1988 |
| EP | 00410147 | 1/1991 |
| EP | 00405376 | 8/1994 |
| JP | 03093057 | 4/1991 |
| WO | WO 02/055697 | 7/2002 |

OTHER PUBLICATIONS

Nijhuis et al. (Journal of Clinical Microbiology, Oct. 2002, vol. 40, no. 10, p. 3666-3670).*
Loens et al. (Journal of Clinical Microbiology, 2003, vol. 43, No. 3, p. 1971-1976).*
Buck et al. (Biotechniques (1999) 27(3):528-536).*
Samuelson et al. (J. Virol. Met., 1998, vol. 71, p. 197-209).*
New England BioLabs Inc. 1998/1999 catalog, p. 121 and p. 284, 1989/1999.
Andewag et al., Improved detection of rhinoviruses in clinical samples by using a newly developed nested reverse transcription-PCR assay. Journal of Clinical Microbiology, 37(3): 524-530, 1999.
Buck et al., Design strategies and performance of custom DNA sequencing primers. BioTechniques, 27(3): 528-536, 1999.
Nijhuis et al., Rapid and sensitive routine detection of all members of the genus Enterovirus in different clinical specimens by real-time PCR. Journal of Clinical Microbiology, 40(10): 3666-3670, 2002.
Loens, et al., "Improved detection of rhinoviruses by nucleic acid sequence-based amplification after nucleotide sequence determination of the 5' noncoding regions of additional rhinovirus strains", J Clin Microbiol. vol. 41. pp. 1971-1976 (2003).
Loens, et al., "Improved detection of rhinoviruses in clinical samples by using a newly developed nested reverse transcription-PCR assay", J Clin Microbiol, vol. 37, pp. 524-30 (1999).
Poelstra, et al., Single tube real time RT PCR assay for detection of enterviruses Abstract of the General Meeting of the American Society for Microbiology, vol. 102, pp. 140 (2002).
Weady, et al., "A sensitive and precise method for detection and quantification of human rhinovirus", Antiviral Research, vol. 50, No. 1, pp. A88 (2001).
Billaud et al. "Detection of rhinovirus and enterovirus in upper respiratory tract samples using a multiplex nested PCR" J. Virol. Methods (2003) 108: 223-228.
Blomqvist et al. "Rapid detection of human rhinoviruses in nasopharyngeal aspirates by a microwell reverse transcription-PCR-hybridization assay." J. Clin. Microbiol. (1999) 37: 2813-2816.
Chapman, et al., "Molecular Detection and Identification of Enteroviruses Using Enzymatic Amplification and Nucleic Acid Hybridization", Journal of Clinical Microbiology, (1990), vol. 28, No. 5, p. 843-850.
Deffernez C., et al., "Amplicon Sequencing and Improved Detection of Human Rhinovirus in Respiratory Samples", Journal of Clinical Microbiology (2004) vol. 42, No. 7, p. 3212-3218.
Hayden F., "Rhinovirus and the lower respiratory tract", Rev. Med. Virol. (2004) 14: 17-31.
Hyypia T., et al. "Molecular diagnosis of human rhinovirus infections: comparison with virus isolation", J. Clin Microbiol. (1998) 36: 2081-2083.
Kares et al. "Real-time PCR for rapid diagnosis of entero- and rhinovirus infections using LightCycler" J Clin Virol. Feb. 2004;29(2):99-104.
Lai, et al., "Evaluation of Real-Time PCR versus PCR with Liquid-Phase Hybridization for Detection of Enterovirus RNA in Cerebrospinal Fluid", Journal of Clinical Microbiology, (2003) vol. 41, No. 7, p. 3133-3141.
Lina, et al., "Multicenter Evaluation of a Commercially Available PCR Assay for Diagnosing Entervirus Infection in a Panel of Cerebrospinal Fluid Specimens", Journal of Clinical Microbiology, (1996) vol. 34, No, 12, p. 3002-3006.
Loens et al. "Improved detection of rhinoviruses by nucleic acid sequence-based amplification after nucleotide sequence determination of the 5' noncoding regions of additional rhinovirus strains", J. Clin. Microbiol. (2003) 41: 1971-1976.
Nijhuis, et al., "Rapid and Sensitive Routine Detection of All Members of the Genus Enterovirus in Different Clinical Specimens by Real-Time PCR", Journal of Clinical Microbiology, (2002) vol. 40, No. 10, p. 3666-3670.

(Continued)

*Primary Examiner* — Stephanie K Mummert
(74) *Attorney, Agent, or Firm* — Foley & Lardner LLP

(57) ABSTRACT

The invention provides methods and compositions for rapid, sensitive, and highly specific nucleic acid-based (e.g., DNA based) detection of human rhinovirus (HRV) in a sample. In general, the methods involve detecting a target nucleic acid having a target sequence of a conserved 5' untranslated region of the HRV genome. The invention also features compositions, including primers, probes, and kits, for use in the methods of the invention.

23 Claims, 8 Drawing Sheets

OTHER PUBLICATIONS

Santti J., et al. "Comparison of PCR primer pairs in the detection of human rhinoviruses in nasopharyngeal aspirates". J. Virol. Methods (1997) 66: 139-147.

Savolainen et al. "Genetic clustering of all 102 human rhinovirus prototype strains: serotype 87 is close to human enterovirus 70", J. General Virol. (2002) 83: 333-340.

Steininger et al. "Early detection of acute rhinovirus infections by rapid reverse transcription-PCR assay." J. Clin. Microbiol. (2001) 39: 129-133.

Non-final Office Action dated Aug. 1, 2007 for U.S. Appl. No. 10/886,517.

Final Office Action dated Jun. 5, 2008 for U.S. Appl. No. 10/886,517.

Non-final Office Action (after the filing of a Notice of Appeal) dated Jan. 29, 2009 for U.S. Appl. No. 10/886,517.

US Office Action on dated Jan. 18, 2007 for U.S. Appl. No. 10/886,517.

Halonen et al., Detection of Enterovirus and Rhinoviruses in Clinical Specimens by PCR and Liquid-Phase Hybridization. Journal of Clinical Microbiology, vol. 33, No. 3, 1995, pp. 648-653, XP002556118.

Lonnrot et al., Diagnosis of Enterovirus and Rhinovirus Infections by RT-PCR and Time-Resolved Fluorometry with Lanthanide Chelate Labeled Probes. Journal of Medical Virology, vol. 59, 1999, pp. 378-384, XP002556117.

Mori et al., Polymerase Chain Reaction and Sequencing for Typing Rhinovirus RNA. Journal of Medical Virology, vol. 44, 1994, pp. 323-329, XP002556119.

Loens et al., Improved detection of Rhinoviruses by nucleic acid sequence-based amplification after nucleotide sequence determination of the 5' noncoding regions of additional rhinovirus strains. Journal of Clinical Microbiology, 41(5): 1971-1976, 2003.

Abdeweg et al., Improved detection of Rhinoviruses in clinical samples by using a newly developed nested reverse transcription-PCR assay. Journal of Clinical Microbiology, 37(3): 524-530, 1999.

Buck et al., Design strategies and performance of custom DNA sequencing primers. Biotechniques, 27(3), 528-536, 1999.

International Search report for PCT Patent Application No. PCT/US05/23400, 2008.

He et al, Primers are Decisive for Sensitivity of PCR, BioTechniques, (1994), 17: 82-87.

Thoelen et al, J Med Virol, (2003), 70(3):424-429.

US Office Action dated Apr. 1, 2011 in U.S. Appl. No. 10/886,517.

* cited by examiner

FIG. 1

RHINO Consensus of the 5' UTR

NCAAGCACTTCTGTTCCCCGGNNNNNNTNNNNNGCTCCACCNATGCCAAAAACAATTNAATCGTTATCCGCAAAGTGACTACGCAAA

GCCTAGTAACATCTTGTAAGATTTTGGTGTCGATCAGGTGCNNNNNATACCCCCAGTAGACCTGGCAGATGANGGCTGGAAATTCC

CCACTGGCGACAGTGTTCCAGCNCTGCGTGGCTGCCTGCCCACNNCTTATNNGGTGTGAAGCCATA

TTTGGACATGGTGTGAAGAGCGCGTGTGCTCACTTNTGAGTCCTCCGGCCCCTGAATGCGGCTAACCTTAACCTGCAGCCATGGCAC
Rhino variations:            SY V R                                 W M YRS FOCUS:    GGTGTGAAGAGASYCVCRTGTGCT         TGAGTCCTCCGGCCCCTGAATG   CCGATTGGAWTTKGGRYSTCG    3' primer
          5' primer       (SEQ ID NO:22)  probe      (SEQ ID NO:23)           (SEQ ID NO:24)

ENTERO:   GGTGYGAAGAGCCTATTGAGCT                     RKARTCCTCCGGCCCCTGAATG  GGCTAATCCTAACYRCGGAGC
                          (SEQ ID NO:25)                     (SEQ ID NO:26)           (SEQ ID NO:27)

ACAATCCAGNTGTGTTTATGGTCGGAATGTAATGAGCAATTGCGGATGGGACNCGACTACTTTGGGTGTCCGTGTTC  (SEQ ID NO:21)

Keys: R = A or G, S = C or G, Y = C or T, W = A or T, M = A or C, K = G or T, V = A, C or G

FIG. 3A

```
                                         5' Forward Primer
                                          G G T G T G A A G
      ------------------+------------------+------------------+-
                       430                440                450
      ------------------+------------------+------------------+-
Rhino:
  342  G G G A C G C C T T A A G T A T G A C A T G G T G T G A A G   af108149
  342  G T G A A G C C A A G G A T T G G A C A G G G T G T G A A G   af108153
  327  G T G A A G C C A A A C A A T G G A C A G G G T G T G A A G   af108165
  331  G T G A A G C C A G A A T T T C G A C A A G G T G T G A A G   af108171
  178  G T G A A G C C A A A T A T T G G A C A A G G T G T G A A G   af542441
  171  G T G A A G C C T T A A T T T G G A C A G G G T G C G A A G   af542444
  187  G T G A A G C C A G A A T T T C G A C A A G G T G T G A A G   af542448
  400  G G G A C G C C C T T T T A A G G A C A T G G T G T G A A G   HRV-B
  337  G T G A A G C C A A A G A T C G G A C A G G G T G T G A A G   HRV-1A
  392  G T G A A G C C A A A G A T T G G A C A G G G T G T G A A G   HRV-1B
  382  G T G A A G C C A A A C A A T G G A C A A G G T G T G A A G   HRV-2
  188  G G G A C G C C C T T T T A T A G A C A T G G T G T G A A G   HRV-6
  331  G A G A A G C C T T A T T A T T G A C A A G G T G T G A A G   HRV-7
  166  A G G A C G C T A - G T A G T G A A C A A G G T G T G A A G   HRV-13
  400  G G G A C G C C C T T T T A A G G A C A T G G T G T G A A G   HRV-14
  386  G T G A A G C C A A G T A T T G G A C A A G G T G T G A A G   HRV-16
  186  G G G A C G C C T T A A T T G T G A C A T G G T G T G A A G   HRV-17
  325  G C G A A G C C A T A C A T T G G A C A A G G T G T G A A G   HRV-21
  324  G T G A A G C C A T A T A T T T T G A C A A G G T G T G A A G   HRV-29
  344  G G G A C G C C T T T T T A T G G A C A T G G T G T G A A G   HRV-37
  178  G T G A A G C C A T T C A T T G G A C A G G G T G A G A A G   HRV-39
  199  A G G A C G C T A - G T A G T G A A C A A G G T G T G A A G   HRV-45
  182  G C G A A G C C A A G T A A C G G A C A G G G T G T G A A G   HRV-51
  191  G G G A C G C C T T A A G T A T G A C A T G G T G T G A A G   HRV-52
  327  G T G A A G C C A T A T A T T T G A C A A G G T G T G A A G   HRV-62
  181  G G G A C G C C C C G A T T G C G A C A C G G G G T G A A G   HRV-69
  181  G G G A C G C C T T A A T T G T G A C A T G G T G C G A A G   HRV-70
  345  G G G A C G C C C T T T C A A T G A C A T G G T G T G A A G   HRV-72
  190  G G G A C G C C T T T C A A G A G A C A T G G T G T G A A G   HRV-84
  164  G T G A A G C C A T A C A T T T G A C A A G G T G T G A A G   HRV-85
  179  G G G A C G C C A A T T T G T T G A C A T G G T G T G A A G   HRV-86
  290  G A G A C G C T A - G A C A T G A A C A A G G T G T G A A G   HRV-87
  178  G G G A C G C C T T A A T T G T G A C A T G G T G T G A A G   HRV-91

Entero:
  396  A G G A C G C T A - G T T G T G A A C A A G G T G T G A A G   Polio 2
  230  A G G A C G C T C T A A T A T G G A C A T G G T G T G A A G   Coxsackie A7
  230  A G G A C G C T C T A A T G C T G A C A T G G T G C G A A G   Coxsackie A9
  400  A G G A C G C T C T A A T A T G G A C A T G G T G C A A A G   Coxsackie A16
  390  G G G A C G C T A - G T T G T G A A C A A G G T G T G A A G   Coxsackie A21
  207  G G G A C G C T T C A A T A C T G A C A C G G T G T G A A G   Coxsackie B1
  394  G G G A C G C T C T A A T A C A G A C A T G G T G C G A A G   Coxsackie B3
  209  G G G A C G C T T C A A T A C T G A C A T G G T G C G A A G   Coxsackie B5
  397  A G G A C G C T C T A A T G T G G A C A T G G T G C G A A G   Entero 71
  400  A G G A C G C T C T A A T A T G G A C A T G G T G C A A A G   Entero A
  394  A G G A C G C T C T A A T A C A G A C A T G G T G C G A A G   Entero-B
```

FIG. 3B

```
                                           Probe
        A S Y C V C R T G T G C T          T G A G T C C T C C G
           (SEQ ID NO:72)
        -------------------+-----------------------+----------------------+-
                          460                     470                    480
        -------------------+-----------------------+----------------------+-
```

Rhino:
```
372  A C C C G C A T G T G C T T A G C T G T G A G T C C T C C G  af108149
372  A G C C G C G T G T G C T C G C T T - T G A G T C C T C C G  af108153
357  A G C C C C G T G T G C T C A T C T - T G A T T C C T C C G  af108165
361  A G C C G C G T G T G C T C A C C T - T G A G T C C T C C G  af108171
208  A G C C G C G T G T G C T C A T C T - T G A G T C C T C C G  af542441
201  A G C C G C G T G T G C T C A T C T - T G A G T C C T C C G  af542444
217  A G C C G C G T G T G C T C A C C T - T G A G T C C T C C G  af542448
430  A C T C G C A T G T G C T T G G T T G T G A G T C C T C C G  HRV-B
367  A G C C G C G T G T G C T C A C T T - T G A G T C C T C C G  HRV-1A
422  A G C C G C G T G T G C T C A C T T - T G A G T C C T C C G  HRV-1B
412  A G C C C C G T G T G C T C G C T T - T G A G T C C T C C G  HRV-2
218  A C T C G C A T G T G C T T G G T T G T G A T T C C T C C G  HRV-6
361  A G C C G C G T G T G C T T G G T G - T G A G T C C T C C G  HRV-7
195  A G C C C A C T G A G C T - A C C T G A G A A T C C T C C G  HRV-13
430  A C T C G C A T G T G C T T G G T T G T G A G T C C T C C G  HRV-14
416  A G C C G C G T G T G C T C A T C T - T G A G T C C T C C G  HRV-16
216  A C C C A C G T G T G C T T A A T T G T G A G T C C T C C G  HRV-17
355  A G C C C C G T G T G C T C A C T T - T G A G T C C T C C G  HRV-21
354  A G C C C C G T G T G C T C A T T T - T G A G T C C T C C G  HRV-29
374  A C T C G C A T G T G C T T G G T T G T G A C T C C T C C G  HRV-37
208  A G C C C A G T G T G C T C A T T T - T G A G T C C T C C G  HRV-39
228  A G C C C A C T G A G C T - A C C T G A G A A T C C T C C G  HRV-45
212  A G C C C C G T G T G C T C G A T T - T G A G T C C T T C G  HRV-51
221  A C C C G C A T G T G C T T A A C T G T G A G T C C T C C G  HRV-52
357  A G C C C C G T G T G C T C A C T T - T G A G T C C T C C G  HRV-62
211  A C C C G C G T G T G C T C A A C T G T G A G A C C T C C G  HRV-69
211  A C C C A C G T G T G C T T A A T T G T G A G T C C T C C G  HRV-70
375  A C T C G C A T G T G C T T G A T T G T G A G T C C G C C G  HRV-72
220  A C T C A A T T G T G C T T G G T T G T G A G T C C T C C G  HRV-84
194  A G C C C C G T G T G C T C A C T T - T G A G T C C T C C G  HRV-85
209  A T C T T A A T G T G C T T G G T T G T G A G T C C T C C G  HRV-86
319  A G T T T A T T G A G C T - A C T A T A G A G T C C T C C G  HRV-87
208  A C C C A C G T G T G C T T A A T T G T G A G T C C T C C G  HRV-91
```

Entero:
```
425  A G C C T A T T G A G C T - A C C T G A G A G T C C T C C G  Polio 2
260  A G T C T A T T G A G C T - A G T T A G T A G T C C T C C G  Coxsackie A7
260  A G T C T A T T G A G C T - A G C T G G T A G T C C T C C G  Coxsackie A9
430  A G T C T A T T G A G C T - A G T T A G T A G T C C T C C G  Coxsackie A16
419  A G C C T A T T G A G C T - A C T C A A G A G T C C T C C G  Coxsackie A21
237  A G T C T A T T G A G C T - A A T T G G T A G T C C T C C G  Coxsackie B1
424  A G T C T A T T G A G C T - A G T T G G T A G T C C T C C G  Coxsackie B3
239  A G T C A A T T G A G C T - A G T T G G T A G T C C T C C G  Coxsackie B5
427  A G C C T A T T G A G C T - A G T T A G T A G T C C T C C G  Entero 71
430  A G T C T A T T G A G C T - A G T T A G T A G T C C T C C G  Entero A
424  A G T C T A T T G A G C T - A G T T G G T A A T C C T C C G  Entero-B
```

FIG. 3C

```
                        3' Reverse Primer (in reverse complement of actual primer)
          G C C C C T G A A T G   G G C T A A C C T W A A M C C Y R S
              (SEQ ID NO:73)
          ---------------+--------------------+--------------------+-
                        490                  500                  510
          ---------------+--------------------+--------------------+-
```

Rhino:
```
    402   G C C C C T G A A T G C G G C T A A C C T A A A C C C T G G   af108149
    401   G C C C C T G A A T G C G G C T A A C C T T A A A C C T G C   af108153
    386   G C C C C T G A A T G C G G C T A A C C T T A A A C C T G C   af108165
    390   G C C C C T G A A T G C G G C T A A C C T T A A A C C C G C   af108171
    237   G C C C C T G A A T G T G G C T A A C C T T A A A C C T G C   af542441
    230   G C C C C T G A A T G C G G C T A A C C T T A A A C C T G C   af542444
    246   G C C C C T G A A T G C G G C T A A C C T T A A A C C C G C   af542448
    460   G C C C C T G A A T G C G G C T A A C C T T A A C C C T A G   HRV-B
    396   G C C C C T G A A T G C G G C T A A C C T T A A A C C T G C   HRV-1A
    451   G C C C C T G A A T G C G G C T A A C C T T A A A C C T G C   HRV-1B
    441   G C C C C T G A A T G T G G C T A A C C T T A A C C C T G C   HRV-2
    248   G C C C C T G A A T G C G G C T A A C C C T A A C C C T G G   HRV-6
    390   G C C C C T G A A T G T G G C T A A C C T T A A C C C T G C   HRV-7
    224   G C C C C T G A A T G C G G C T A A T C C C A A C C A C G G   HRV-13
    460   G C C C C T G A A T G C G G C T A A C C T T A A C C C T A G   HRV-14
    445   G C C C C T G A A T G T G G C T A A C C T T A A A C C T G C   HRV-16
    246   G C C C C T G A A T G C G G C T A A C C T A A A C C C T G G   HRV-17
    384   G C C C C T G A A T G T G G C T A A C C T T A A C C C T G C   HRV-21
    383   G C C C C T G A A T G T G G C T A A C C T T A A C C C T G C   HRV-29
    404   G C C C C T G A A T G C G G C T A A C C T T A A C C C C G G   HRV-37
    237   G C C C C T G A A T G T G G C T A A N C T T A A A C C T G N   HRV-39
    257   G C C C C T G A A T G C G G C T A A T C C C A A C C A C G G   HRV-45
    241   G C C C C T G A A T G T G G C T A A C C T T A A C C C T G C   HRV-51
    251   G C C C C T G A A T G C G G C T A A C C T T A A C C C T G G   HRV-52
    386   G C C C C T G A A T G T G G C T A A C C T T A A C C C T G C   HRV-62
    241   G C C C C T G A A T G C G G C T A A C C T A A A C C C T G G   HRV-69
    241   G C C C C G A A T G C G G C T A A C C T A A A C C C C G G     HRV-70
    405   G C C C C T G A A T G C G G C T A A C C C T A A C C C T G G   HRV-72
    250   G C C C C T G A A T G C G G C T A A C C T T A A A C C C G G   HRV-84
    223   G C C C C T G A A T G T G G C T A A C C T T A A C C C T G C   HRV-85
    239   G C C C C T G A A T G C G G C T A A C C T T A A C C C C G G   HRV-86
    348   G C C C C T G A A T G C G G C T A A T C C T A A C C A T G G   HRV-87
    238   G C C C C T G A A T G C G G C T A A C C T A A A C C C T G G   HRV-91
```

Entero:
```
    454   G C C C C T G A A T G C G G C T A A T C C T A A C C A C G G   Polio 2
    289   G C C C C T G A A T G C G G C T A A T C C T A A C T G C G G   Coxsackie A7
    289   G C C C C T G A A T G C G G C T A A T C C C A A C T G C G G   Coxsackie A9
    459   G C C C C T G A A T G C G G C T A A T C C T A A C T G C G G   Coxsackie A16
    448   G C C C C T G A A T G C G G C T A A T C C T A A C C A C G G   Coxsackie A21
    266   G C C C C T G A A T G C G G C T A A T C C T A A C T G C G G   Coxsackie B1
    453   G C C C C T G A A T G C G G C T A A T C C T A A C T G C G G   Coxsackie B3
    268   G C C C C T G A A T G C G G C T A A T C C T A A C T G T G G   Coxsackie B5
    456   G C C C C T G A A T G C G G C T A A T C C T A A C T G C G G   Entero 71
    459   G C C C C T G A A T G C G G C T A A T C C T A A C T G C G G   Entero A
    453   G C C C C T G A A T G C G G C T A A T C C T A A C T G C G G   Entero-B
```

FIG. 3D

```
     A G C (SEQ ID NO:74)
     ----------------+----------------+----------------+-
                    520              530              540
     ----------------+----------------+----------------+-

Rhino:
  432  A G C C T T G G A G C A C A A G C C A G - T G C T T G C A A   af108149(SEQ ID NO:28)
  431  A G C C A T G G C T C A T A A G C C A A - T G A G T T T A T   af108153(SEQ ID NO:29)
  416  A G C C A T T G C T C A C A A T C C A G - T G A G T T A G T   af108165(SEQ ID NO:30)
  420  A G C C A T G G T C C A C A A A C C A G - T G G A T G T A T   af108171(SEQ ID NO:31)
  267  A G C C A G T G C G C A C A A T C C A G - T G T G T A G C T   af542441(SEQ ID NO:32)
  260  A G C C A T T G T T T G C A A T C C A G - C A A A T A T G T   af542444(SEQ ID NO:33)
  276  A G C C A T G G T C C A C A A A C C A G - T G G A T G T A T   af542448(SEQ ID NO:34)
  490  A G C C T T A T G C C A C G A T C C A G - T G G T T G T A A   HRV-B(SEQ ID NO:35)
  426  A G C C A T G G C T C A T A A G C C A A - T G A G T T T A T   HRV-1A(SEQ ID NO:36)
  481  A G C C A T G G C T C A T A A A C C A A - T G A G C T T A T   HRV-1B(SEQ ID NO:37)
  471  A G C T A G A G C A C G T A A C C C A A - T G T G T A T C T   HRV-2(SEQ ID NO:38)
  278  A G C C T T G T G T T A C A A A C C A G - T A A T A T T A A   HRV-6(SEQ ID NO:39)
  420  A G C C A T T G C T T C A T A A T C C A A - T G A G T T A G T   HRV-7(SEQ ID NO:40)
  254  A G C A G G T A A T C G C A A A C C A G - C G G T C A G C C   HRV-13(SEQ ID NO:41)
  490  A G C C T T A T G C C A C G A T C C A G - T G G T T G T A A   HRV-14(SEQ ID NO:42)
  475  A G C C A G T G C A C A C A A T C C A G - T G T G T A G C T   HRV-16(SEQ ID NO:43)
  276  A G C C T T G A G A C A C A A T C C A G - T G T T G G C A A   HRV-17(SEQ ID NO:44)
  414  A G C T A G T G C A T G T A A T C C A A - C A T G T T G C T   HRV-21(SEQ ID NO:45)
  413  A G C T A G T G C A T G C A A T C C A G - C A T G T T G C T   HRV-29(SEQ ID NO:46)
  434  A G C C C T G T G T T G C A A T C C A G - T A A C A T T A G   HRV-37(SEQ ID NO:47)
  267  A G N C A A T G C A C A C A A T C C A G - N G T G T A T T T   HRV-39(SEQ ID NO:48)
  287  A G C A G G T A A T C G C A A A C C A G - C G G T C A G C C   HRV-45(SEQ ID NO:49)
  271  A G C T A G G G C A C A C A A T C C A G - T G T G T A T C T   HRV-51(SEQ ID NO:50)
  281  A G C C T T G G A G T A C A A T C C A G - T G C T A A C A A   HRV-52(SEQ ID NO:51)
  416  A G C T A G T G T A T G T A A T C C A A - C A T A T G G C T   HRV-62(SEQ ID NO:52)
  271  A G C C T C G A A A C A C A A C C C A G A T G T T C G C A A   HRV-69(SEQ ID NO:53)
  271  A G C C T T G A G A C A C A A T C C A G - T G T T A G C A A   HRV-70(SEQ ID NO:54)
  435  A G C C T T G C A C C A C A A T C C A G - T G G T G T C T G   HRV-72(SEQ ID NO:55)
  280  A T C C A T G C T A T G C A A A C C A G - C A T A G T T A T   HRV-84(SEQ ID NO:56)
  253  A G N T G G T G C A T G T A A T C C A A - C A T G T T G C T   HRV-85(SEQ ID NO:57)
  269  A G C C T T G T G T C A C A A G C C A G - T G A C A T T A A   HRV-86(SEQ ID NO:58)
  378  A G C A A G T G C T C A C A A A C C A G - T G G G T T G C T   HRV-87(SEQ ID NO:59)
  268  A G C C T T G A A A C A C A A T C C A G - T G T T A G C A A   HRV-91(SEQ ID NO:60)

Entero:
  484  A G C A G G C A G T G G C A A T C C A G - C G A C C A G C C   Polio 2(SEQ ID NO:61)
  319  A G C A C G T A C C T C C A A T C C A G - G A G G T G G C G   Coxsackie A7(SEQ ID NO:62)
  319  A G C A C G C A C C C T C A A A C C A G - G G G G C A G C G   Coxsackie A9(SEQ ID NO:63)
  489  A G C A C A T A C C C T C G A C C C A G - G G G G C A G T G   Coxsackie A16(SEQ ID NO:64)
  478  A G C A A T C G C T C A C G A C C C A G - T G A G T A G G T   Coxsackie A21(SEQ ID NO:65)
  296  A G C A G A T A C C C A C G C G C C A G - T G G G C A G T C   Coxsackie B1(SEQ ID NO:66)
  483  A G C A C A C A C C C T C A A G C C A G - A G G G C A G T G   Coxsackie B3(SEQ ID NO:67)
  298  A G C A G A T A C C C A C A G A C C C A G - T G G G C A G T C   Coxsackie B5(SEQ ID NO:68)
  486  A G C A C A T G C C T T C A A C C C A G - A G G G T A G T G   Entero 71(SEQ ID NO:69)
  489  A G C A C A T A C C C T C G A C C C A G - G G G G C A G T G   Entero A(SEQ ID NO:70)
  483  A G C A C A T A C C C T C A A A C C A G - G G G G C A G T G   Entero-B(SEQ ID NO:71)
```

METHODS AND COMPOSITIONS FOR DETECTING RHINOVIRUSES

CROSS REFERENCE TO RELATED PATENT APPLICATIONS

This application is a divisional of U.S. patent application Ser. No. 10/886,517, filed on Jul. 6, 2004. The prior filed application is incorporated herein by reference in its entirety.

FIELD OF THE INVENTION

The invention relates to methods and compositions for use in detection of a virus, particularly to nucleic acid-based assays for detecting rhinovirus.

BACKGROUND OF THE INVENTION

Human rhinoviruses (HRVs) are the most frequent cause of acute upper respiratory tract infections in humans and are usually associated with the common cold. Common colds caused by HRV occur throughout the year, with peaks of incidence in the autumn and spring, are one of the main reasons for absences from work and school, which have major economic impact. Rhinoviruses can also cause lower respiratory tract infections resulting in severe disease in children, in the elderly and in immunosuppressed patients.

The HRVs, which include over 100 different serotypes, are small, non-enveloped, positive (+)-strand RNA viruses, HRVs are one of the six genera of Picornaviridae, which also includes enteroviruses (EVs). Reverse transcription-polymerase chain reaction (RT-PCR) has been developed in the past few years for the detection of the HRVs in clinical specimens (see, e.g., Billaud et al. (2003) J. Virol. Methods 108: 223-228; Blomqvist et al. (1999) J. Clin, Microbiol. 37:2813-2816; Kares et al. (2003) J Clin Virol. 2004 February; 29(2): 99-104; Loens et al. (2003) J. Clin. Microbiol. 41: 1971-1976; Savolainen et al. (2002) J. General Virol. 83: 333-340; Steininger et al. (2001) J. Clin. Microbiol. 39: 129-133). Most of these RT-PCR methods take advantage of the conserved sequences in the 5' noncoding region of the picornavirus genome.

The ability to detect HRV specifically—and particularly avoiding false positives that can result due to the relatedness of HRV and EV—is important to both diagnosis and selection of appropriate available therapy. Specific assays for HRV are also important for development of new drugs. For example, it is critical for clinical trial design that the participants be correctly identified as having an HRV infection where the trial is designed to evaluate a drug for use in treatment of HRV infections. Moreover, in other clinical trials, it may be important to exclude individuals infected with HRV. Further, the HRV detection assays must be simple to perform, provide easily interpreted results, and be relatively inexpensive to make them practical for use.

Conventional methods of differentiation of HRVs from EVs has been done either by virus neutralization assay, by selection with HRV-specific primer pairs, by distinguishing the amplification products of the two viruses based on differences in size, by sequencing the amplification products and comparing the sequence to known HRV and EV sequences, or by hybridization using HRV or EV-specific probes. These approaches can be time-consuming, expensive, and/or require a skilled technician who has experience in interpreting assay results accurately.

There remains a need in the field for methods for detecting RVs in a manner that is rapid, sensitive and specific, particularly with respect to the ability to distinguish an RV from an EV.

The present invention addresses these needs.

Literature

Literature of interest includes:

Billaud et al. (2003) "Detection of rhinovirus and enterovirus in upper respiratory tract samples using a multiplex nested PCR" J. Virol. Methods 108: 223-228; Blomqvist et al. (1999) "Rapid detection of human rhinoviruses in nasopharyngeal aspirates by a microwell reverse transcription-PCR-hybridization assay." J. Clin. Microbiol. 37: 2813-2816; Hyypia T., et al. (1998). Molecular diagnosis of human rhinovirus infections: comparison with virus isolation. J. Clin Microbiol. 36: 2081-2083; Kares et al. (2003) "Real-time PCR for rapid diagnosis of entero- and rhinovirus infections using LightCycler" J Clin Virol. 2004 February; 29(2):99-104; Loens et al. (2003) "Improved detection of rhinoviruses by nucleic acid sequence-based amplification after nucleotide sequence determination of the 5' noncoding regions of additional rhinovirus strains." J. Clin. Microbiol. 41: 1971-1976; Santti J., et al. (1997). Comparison of PCR primer pairs in the detection of human rhinoviruses in nasopharyngeal aspirates. J. Virol. Methods 66: 139-147; Savolainen et al. (2002) "Genetic clustering of all 102 human rhinovirus prototype strains: serotype 87 is close to human enterovirus 70." J. General Virol. 83: 333-340; Steininger et al. (2001) "Early detection of acute rhinovirus infections by rapid reverse transcription-PCR assay." J. Clin. Microbiol. 39: 129-133; and U.S. Publication No. US2002/0142294.

SUMMARY OF THE INVENTION

The invention provides methods and compositions for rapid, sensitive, and highly specific nucleic acid-based (e.g., DNA based) detection of human rhinovirus (HRV) in a sample. In general, the methods involve detecting a target nucleic acid having a target sequence of a conserved 5' untranslated region of the HRV genome. The invention also features compositions, including primers, probes, and kits, for use in the methods of the invention.

An advantage of the invention is that it provides for detection of most serotypes of HRV while avoiding detection of viruses that are closely related genetically. Thus, the invention decreases the incidence of false negatives.

Another advantage of the invention is that decreases the incidence of false positives that can result from detection of the closely genetically related virus, enterovirus (EV).

Still another advantage is that the invention requires detection of a relatively short target sequence. This can be particularly advantageous where the assay uses amplification-based technology, such as real-time PCR.

The present invention can be developed into assays or manufactured into kits to be use in reference laboratories or hospitals for the diagnostics of rhinovirus which causes common colds. Common colds caused by HRV occur throughout the year, with peaks of incidence in the autumn and spring and it is one of the main reasons for short time absence from work and school, with major economical impact. The assay can also be utilized in the development and clinical trials of therapeutic drugs for treating diseases caused by rhin virus infection.

These and other advantages will be readily apparent to the ordinarily skilled artisan upon reading the present specification.

BRIEF DESCRIPTION OF THE DRAWINGS

FIG. 1 is a schematic showing the target region of human rhinovirus (HRV) detected according to the invention. The target region lies within the consensus sequence of the 5' UTR of HRV genome.

FIGS. 3A-3D are schematics showing an alignment of sequences from the 5' UTR target region of different isolates of HRV, enterovirus (EV), poliovirus, and coxsackie virus isolates sequences. The references on the right side of each sequence indicate the GenBank accession no. and/or virus from which the sequence is derived. Numbering on the left side of the figure refers to the starting nucleotide within the corresponding sequence. Viruses tested using the methods of the invention appear as single underlining (HRV) and double underlining (EV), respectively. Highlighted nucleotides refer to positions that deviated from the primer or probe sequence used in the assay.

DEFINITIONS

Figure 2A:
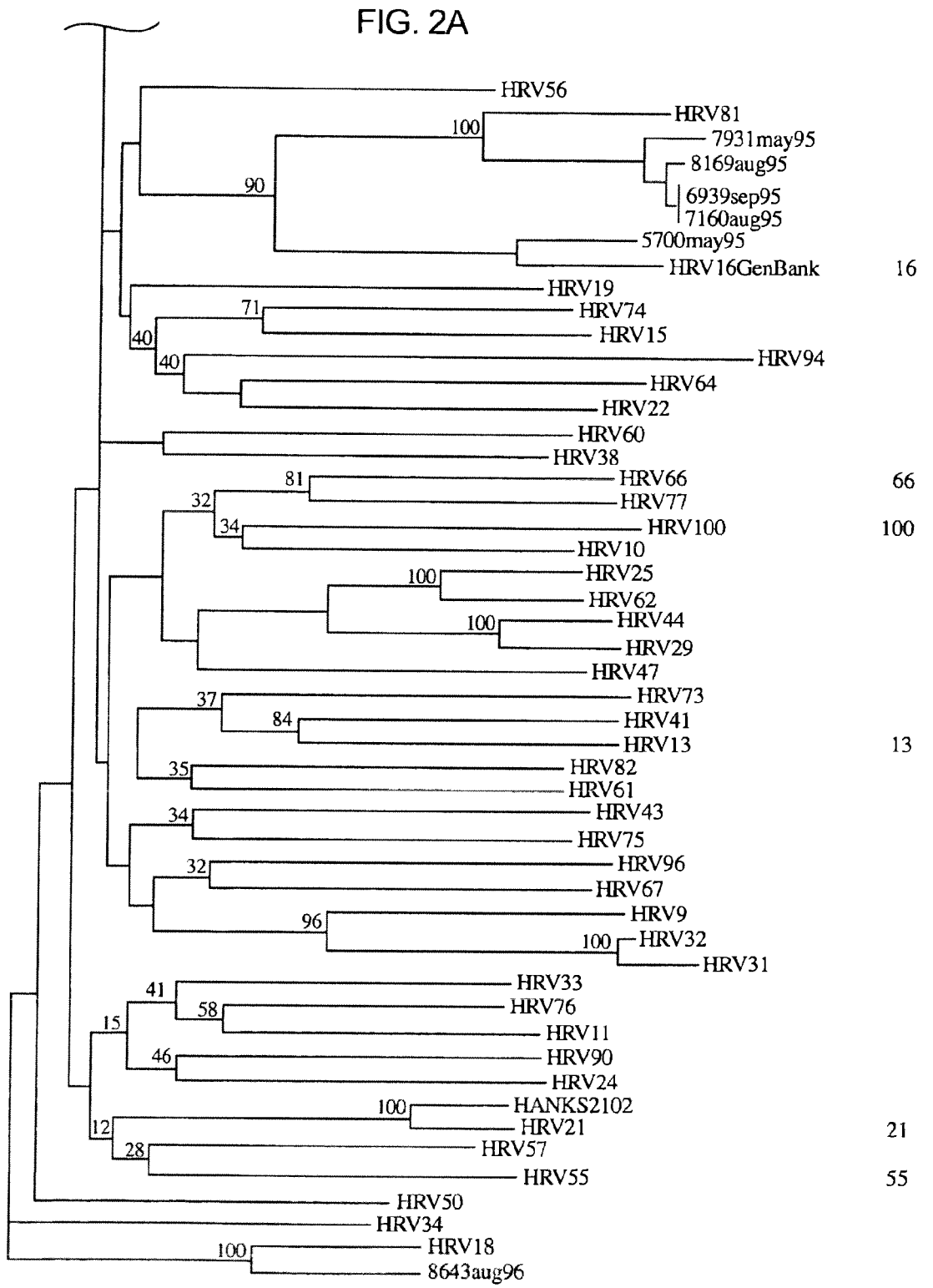
FIGS. 2A, 2B, and 2C are dendograms showing the genetic relationships of various HRV serotypes belonging to Group A and Group B HRV families. HRVs detected according to the methods of the invention are indicated by the numbers to the right of each dendogram (e.g., "88" indicates that the assay was used to detect HRV serotype HRV88).

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

Unless specifically indicated otherwise, there is no intended distinction in length between the terms "polynucleotide," "oligonucleotide," "nucleic acid" and "nucleic acid molecule" and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

Throughout the specification, abbreviations are used to refer to nucleotides (also referred to as bases), including abbreviations that refer to multiple nucleotides. As used herein, G=guanine, A=adenine, T=thymine, C=cytosine, and U=uracil. In addition, R=a purine nucleotide (A or G); Y=a pyrimidine nucleotide (C or T (U)); S=C or G; W=A or T (U); M=A or C; K=G or T (U); V=A, C or G; and N=any nucleotide (A, T (U), C, or G). Nucleotides can be referred to throughout using lower or upper case letters. It is also understood that nucleotides sequences provided for DNA in the specification also represent nucleotide sequences for RNA, where T is substituted by U.

The terms "deoxyribonucleic acid" and "DNA" as used herein mean a polymer composed of deoxyribonucleotides.

The terms "ribonucleic acid" and "RNA" as used herein refer to a polymer composed of ribonucleotides. Where sequences of a nucleic acid are provided using nucleotides of a DNA sequence, it is understood that such sequences encompass complementary DNA sequences and further also encompass RNA sequences based on the given DNA sequence or its complement, where uracil (U) replaces thymine (T) in the DNA sequence or its complement. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which the recited material is unaccompanied by at least some of the material with which it is normally associated in its natural state, preferably constituting at least about 0.5%, more preferably at least about 5% by weight of the total protein in a given sample. For example, the term "isolated" with respect to a polynucleotide generally refers to a nucleic acid molecule devoid, in whole or part, of sequences normally associated with it in nature; or a sequence, as it exists in nature, but having heterologous sequences in association therewith; or a molecule disassociated from the chromosome.

"Purified" as used herein means that the recited material comprises at least about 75% by weight of the total protein, with at least about 80% being preferred, and at least about 90% being particularly preferred. As used herein, the term "substantially pure" refers to a compound that is removed from its natural environment and is at least 60% free, preferably 75% free, and most preferably 90% free from other components with which it is naturally associated.

A polynucleotide "derived from" or "specific for" a designated sequence, such as a target sequence of a target nucleic acid, refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are: derived from" or "specific for" a designated sequence include polynucleotides that are in a sense or an antisense orientations relative to the original polynucleotide.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%, at least about 85%, preferably at least about 90%, and most preferably at least about 95% or at least about 98% sequence similarity over a defined length of the molecules. As used herein, substantially homologous also refers to sequences showing complete Identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as LASERGENE from DNASTAR, Inc; and ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence homology are available in the Wisconsin Sequence Analysis Package, Version 8 (available from Genetics Computer Group, Madison, Wis.) for example, the BEST-FIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code-standard; filter=none; strand=both; cutoff=60; expect=10; Matrix=BLOSUM62; Descriptions-50 sequences; sort by =HIGH SCORE; Databases-non-redundant, GenBank-EMBL DDBJ+PDB+GenBank CDS translations+Swiss protein+Spupdate+PIR. Details of these programs can be found on the internet on a website sponsored by the National Center for Biotechnology Information (NCBI) and the National Library of Medicine (see www.ncbi.nlm.gov/cgi-bin/BLAST).

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule refers to a polynucleotide of genomic, cDNA, mammalian, bacterial, viral, semisynthetic, synthetic or other origin which, by virtue of its origin, manipulation, or both is not associated with all or a portion of the polynucleotide with which it is associated in nature. The term "recombinant" as used with respect to a protein or polypeptide means a polypeptide produced by expression of a recombinant polynucleotide.

A "control element" refers to a polynucleotide sequence which aids in the transcription and/or translation of a nucleotide sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for or facilitate the transcription and translation of a coding sequence in a host cell.

A "DNA-dependent DNA polymerase" is an enzyme that synthesizes a complementary DNA copy from a DNA template. Examples include DNA polymerase I from E. coli and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

A "DNA-dependent RNA polymerase" or a "transcriptase" is an enzyme that synthesizes multiple RNA copies from a double-stranded or partially-double stranded DNA molecule having a (usually double-stranded) promoter sequence. The RNA molecules ("transcripts") are synthesized in the 5' to 3' direction beginning at a specific position just downstream of the promoter. Examples of transcriptases are the DNA-dependent RNA polymerase from *E. coli* and bacteriophages T7, T3, and SP6.

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

"RNAse H" is an enzyme that degrades the RNA portion of an RNA:DNA duplex. These enzymes may be endonucleases or exonucleases. Most reverse transcriptase enzymes normally contain an RNAse H activity in addition to their polymerase activity. However, other sources of the RNAse H are available without an associated polymerase activity. RNA degradation mediated by an RNAse H may result in separation of RNA from a RNA:DNA complex, or the RNAse H may cut the RNA at various locations such that portions of the RNA melt off or permit enzymes to unwind portions of the RNA.

As used herein, the term "target nucleic acid region" or "target nucleic acid" or "target molecules" refers to a nucleic acid molecule with a "target sequence" to be detected (e.g., by amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" refers to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using, the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length, more usually not more than about 10, 12, 15, 20, 21, 22, 23, 24, 25, 26, 27, 28, 29, or 30 nucleotides in length, still more usually not more than about 10, 12, 15, 20, 21, 22, 23, 24, or 25 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, that contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are usually are in the range of between 8 to 100 nucleotides in length, such as 8 to 75, 10 to 74, 12 to 72, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. The typical probe is in the range of between 10-50 nucleotides long, such as 15-45, 18-40, 20-30, 21-28, 22-25 and so on, and any length between the stated ranges. In some embodiments, the probes are usually not more than about 10, 12, 15, 20, 21, 22, 23, 24, 25, 26, 27, 28, 29, 30, 35, 40, 45, 50, 55, 60, 65, or 70 nucleotides in length, more usually not more than about 10, 12, 15, 20, 21, 22, 13, 24, 25, 26, 27, 28, 29, 30, 35, or 40 nucleotides in length, still more usually not more than about 10, 12, 15, 20, 21, 22, 23, 24, or 25 nucleotides in length.

Probes contemplated herein include probes that include a detectable label. For example, when an "oligonucleotide probe" is to be used in a 5' nuclease assay, such as the TaqMan™ assay, the probe includes at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences, Put another way, the term "stringent hybridization conditions" as used herein refers to conditions that are compatible to produce duplexes between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

By "selectively bind" is meant that the molecule binds preferentially to the target of interest or binds with greater affinity to the target than to other molecules. For example, a DNA molecule will bind to a substantially complementary sequence and not to unrelated sequences.

A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50.° C. or about 55° C. to about 60° C.; or, a salt concentration of about 0.15 M NaCl at 72° C. for about 15 minutes; or, a salt concentration of about 0.2×SSC at a temperature of at least about 50° C. or about 55.° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37. ° C. (for 14-base oligos), 48. ° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$, than those having an abundance of AT base pairs. Separated complementary strands of DNA spontaneously reassociate or anneal to form duplex DNA when the temperature is lowered below the $T_m$. The highest rate of nucleic acid hybridization occurs approximately 25 .degree. C. below the $T_m$. The $T_m$ may be estimated using the following relationship: $T_m = 69.3 + 0.41$ (GC) % (Marmur et al. (1962) J. Mol. Biol. 5:109-118).

As used herein, a "biological sample" refers to a sample of tissue or fluid isolated from a subject, which in the context of the invention generally refers to samples suspected of containing nucleic acid and/or viral particles of human rhinovirus, which samples, after optional processing, can be analyzed in an in vitro assay. Typical samples of interest include, but are not necessarily limited to, respiratory secretions (e.g., samples obtained from fluids or tissue of nasal passages, lung, and the like), blood, plasma, serum, blood cells, fecal matter, urine, tears, saliva, milk, organs, biopsies, and secretions of the intestinal and respiratory tracts. Samples also include samples of in vitro cell culture constituents including but not limited to conditioned media resulting from the growth of cells and tissues in culture medium, e.g., recombinant cells, and cell components.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and or determining whether it is present or absent. As used herein, the terms "determining," "measuring," and "assessing," and "assaying" are used interchangeably and include both quantitative and qualitative determinations.

In the context of the methods involving nucleic acid-based amplification of a target sequence, the term "reference range" refers to a range of $C_T$ (threshold cycle) values from HRV-negative specimens representative of results that are deemed to indicate that the sample (e.g., a patient specimen) is HRV virus-negative.

In the context of the methods involving nucleic acid-based amplification of a target sequence, the term "reportable range" refers to a range of $C_T$ values generated by HRV-positive specimens that are representative of results to be reported as HRV-positive patient specimens.

"Analytical specificity" as used herein refers to the ability of a detection system to specifically detect the target virus and not detect other related viruses, or pathogenic or commensal flora found in the specimen types being validated. For example, "analytical specificity" in reference to assays using HRV primers and a probe refers to the ability of this detection system to specifically amplify and detect the target virus and not detect other related viruses, or pathogenic or commensal flora found in the specimen types being validated.

"Analytical sensitivity" in the context of the methods involving nucleic acid-based amplification of a target sequence refers to the lowest measurable amount of HRV virus target DNA that can be detected for each specimen type validated.

"Precision" refers to the ability of an assay to reproducibly generate the same or comparable result for a given sample.

"Accuracy" refers to the ability of an assay to correctly detect a target molecule in a blinded panel containing both positive and negative specimens.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to a "primer" includes a plurality of such primers and reference to "primer" includes reference to one or more the primers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The practice of the present invention will employ, unless otherwise indicated, conventional methods of chemistry, biochemistry, recombinant DNA techniques and virology, within the skill of the art. Such techniques are explained fully in the literature. See, e.g., Fundamental Virology, 2nd Edition, vol. I & II (B. N. Fields and D. M. Knipe, eds.); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Oligonucleotide Synthesis (N. Gait, ed., 1984); A Practical Guide to Molecular Cloning (1984).

The invention will now be described in more detail.

DETAILED DESCRIPTION OF THE INVENTION

The invention is based on the discovery of a conserved consensus sequence within the 5'-UTR of the human rhinovirus (HRV) genome that can serve as a target sequence for detection of HRV in a sample, particularly a biological sample, with specificity and sensitivity. In particular detection of the target sequence allows for detection of HRV while avoiding detection of closely related enterovirus (EV), which is also a Picronaviridae. The specificity and simplicity of these assays facilitate rapid, reliable and inexpensive assays for detection of HRV across HRV serotypes and subgroups.

Figure 2B:
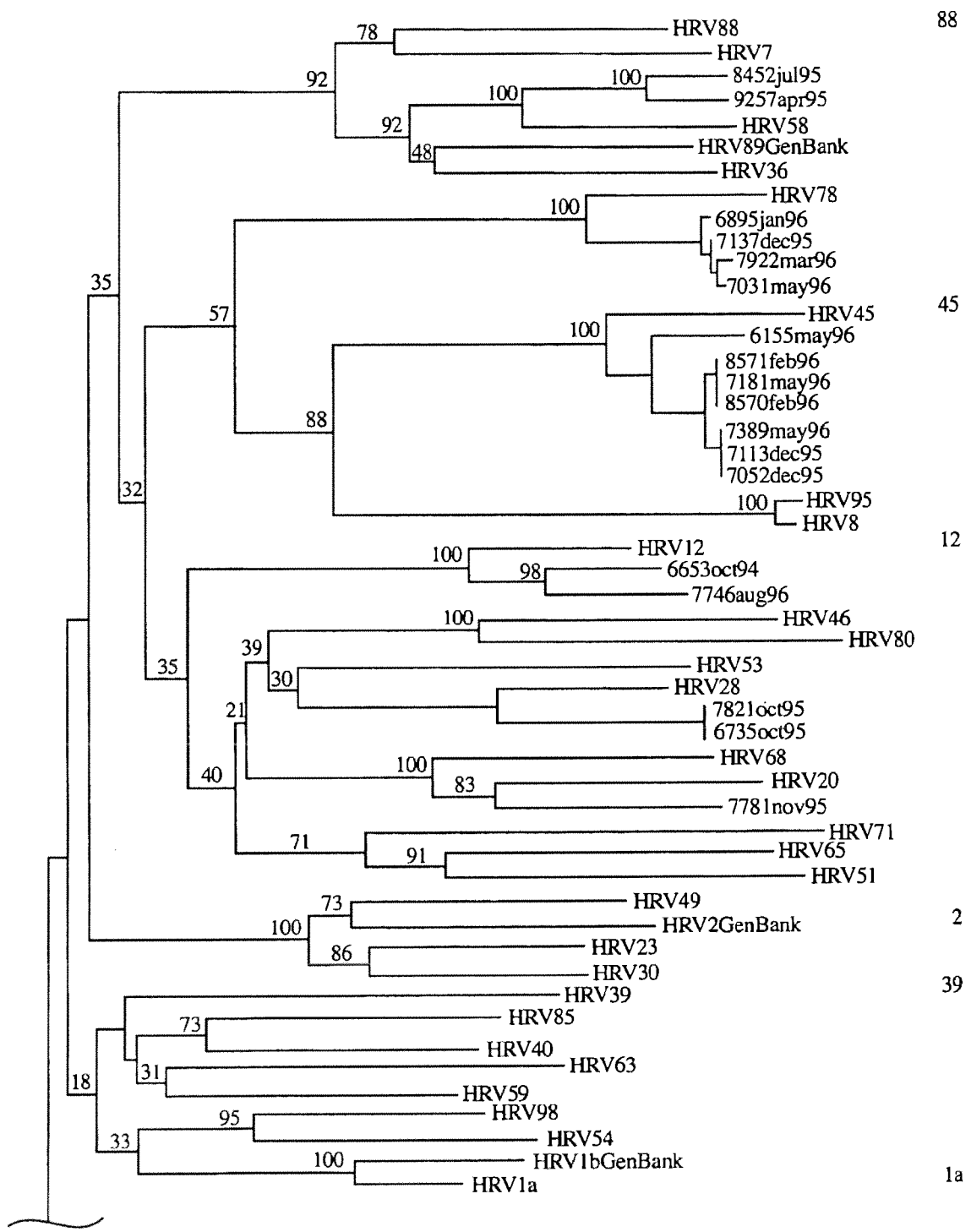
Figure 2C:
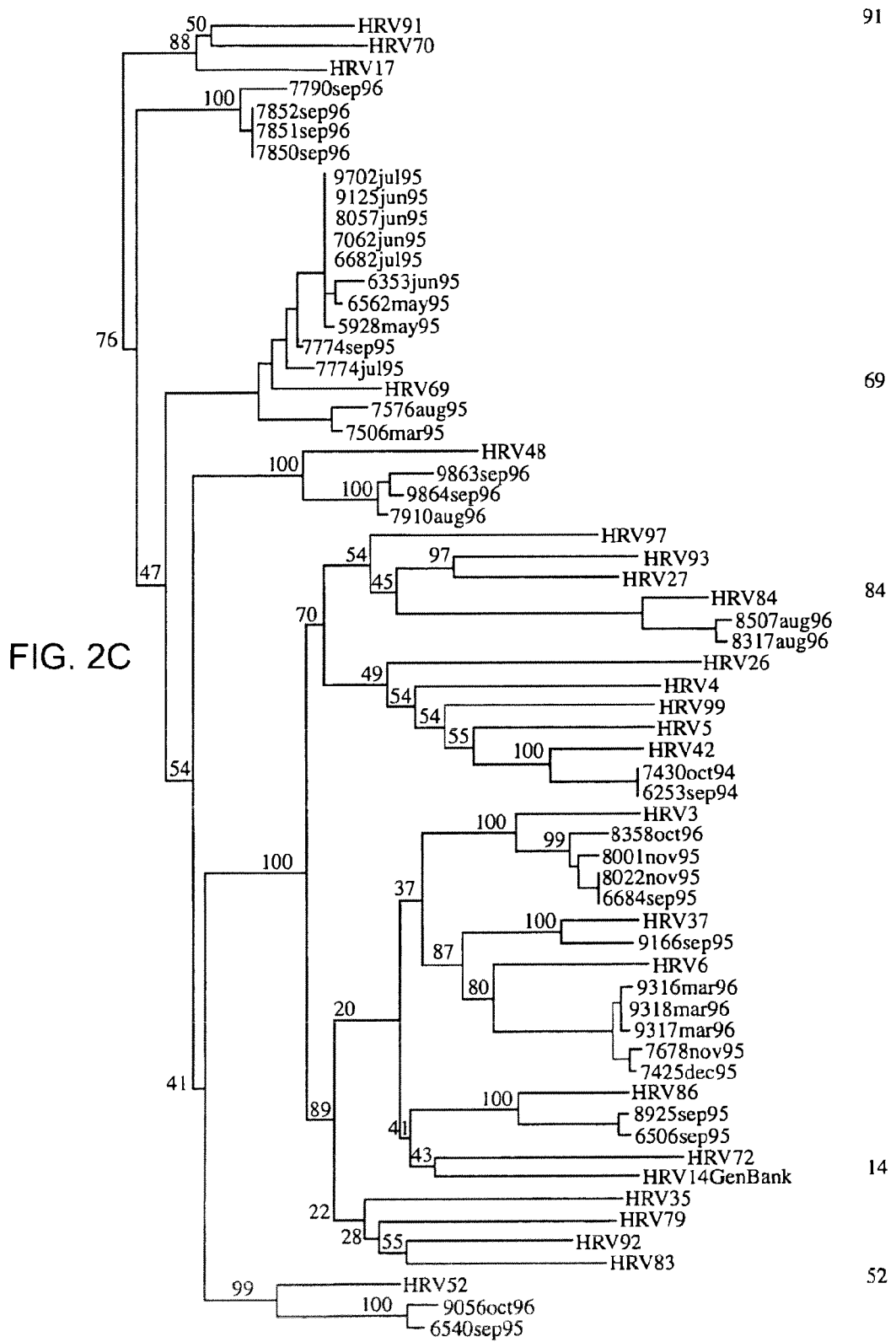

The invention provides methods and compositions that allow sensitive detection of HRV across a wide range of serotypes, while at the same time providing specific detection that avoids false positives that can result from detection of EV. For example, in one embodiment exemplified in FIG. 1, the inventors successfully detected 17 of the 18 HRV serotypes tested. As illustrated by the dendograms in FIGS. 2A, 2B, and 2C, the HRV serotypes detected in the assay represented entire subgroups of the rhinovirus classification. In fact, the one HRV serotype that was not detected using the assay is very closely related to EVs.

We note that the sequences provided herein, and particularly the consensus sequences, are provided as DNA sequences. It is understood that the DNA sequences provided may be single stranded or double-stranded, and as such the description of the DNA sequences below is intended to also provide description of the complementary sequence as well.

Furthermore, since HRV is an RNA virus, it is also to be understood that the DNA sequences further describe single- and double-stranded RNA, and thus, with substitution of uracil (U) for thymine (T) in the sequences provides description of an RNA sequence as well as its complement.

The compositions and methods of the invention will now be described in more detail.

Target Sequence for Detection of HRV

A target nucleic acid sequence region that is highly conserved across many HRV serotypes, which are representative of different HRV subgroups, is found within a region of less than about 100 nucleotides, more specifically about 75 nucleotides, even more specifically 72 nucleotides, within the 5'UTR of HRV. The target sequence was identified by alignment of the sequences of this region from 33 HRV isolates representing different HRV subgroups, as well as the sequences of 11 different enteroviruses, including coxsackie, polio, and enterovirus (see FIGS. 3A-3D). The inventors discovered a consensus target sequence for HRV, which accounts for the variations between HRV serotypes in this region, as follows:

(SEQ ID NO:1)
GGTGTGAAGA syCvCrTGTG CTCACTTNTG AGTCCTCCGG

CCCCTGAATG CGGCTAACCT wAAmCCyrsA GC where the nucleotides in lower case represent nucleotides at variant positions in the HRV target sequence. It is to be understood throughout that since HRV is an RNA virus, the target sequence in the HRV genome contains uracil (U) in lieu of thymine (T). Thus the HRV genomic sequence described above would be:

(SEQ ID NO:2)
GGUGUGAAGA syCvCrUGUG CUCACUUNUG AGUCCUCCGG

CCCCUGAAUG CGGCUAACCU wAAmCCyrsA GC where "y" in this context can be C or U and "w" in this context can be A or U.

In one embodiment, the invention provides for specific detection of HRV while avoiding amplification of a detectable or a significant amount of nucleic acid of a non-HRV picornavirus, with little or no detection of EV being of particular interest. In this embodiment, the invention provides for detection of different rhinovirus with different target nucleic acid sequences while not substantially compromising the assay's feature in avoiding false negatives. The inventors have found that in the EV sequence corresponding to the target sequence of HRV, EV has the following sequence:

(SEQ ID NO:3)
GGTGyGAAGA GCCtatTGaG CTCACTTNrk ArTCCTCCGG

CCCCTGAATG CGGCTAAtc TAACyrCGGA GC or a complement thereof, where nucleotides in highlighted and in lower case represent variant nucleotides among EV isolates analyzed or nucleotides that can differ relative to the nucleotide in the corresponding position in the sequence of HRV.

The differences, as well as the possible matches in sequence between HRV and EV isolates can be taken into account in order to provide for specific detection of HRV nucleic acid in samples having or suspected of having EV nucleic acid. The inventors have found that in the HRV target sequence (SEQ ID NOS:4 and 5)
GGTGX$_1$GAAGA X$_2$X$_3$CX$_4$X$_5$X$_6$TGX$_7$G CTCACTTNT X$_8$X$_9$A

X$_{10}$TCCTCCGG CCCCTGAATG CGGCTAAX$_{11}$CX$_{12}$ X$_{13}$AAX$_{14}$

X$_{15}$X$_{16}$X$_{17}$ X$_{18}$X$_{19}$A GC (which in the genome is RNA) the residues among HRV and EV isolates indicated are as follows:

| Nucleotide | In HRV isolates (SEQ ID NO: 4), this residue is | In EV isolates (SEQ ID NO: 5), this residue is | An amplified product from HRV (or, shown in parentheses, an amplified product from EV) |
|---|---|---|---|
| $X_1$ | T | C or T | May have T (or A in the complementary strand), but not C (or G in the complementary strand) |
| $X_2$ | G or C | G | |
| $X_3$ | C or T | C | (EV amplicons will not have T (or A in the complementary strand)) |
| $X_4$ | A, C, or G | T | (EV amplicons will not have C or G) |
| $X_5$ | C | A | May have C (or G in the complementary strand), but not A (or T in the complementary strand) |
| $X_6$ | G or A | T | May have G or A, but not T (or A in the complementary strand) |
| $X_7$ | T | A | |
| $X_8$ | T | A or G | May have T (or A in the complementary strand), but not G (or C in the complementary strand) |
| $X_9$ | G | G or T | May have G (or C in the complementary strand) but not T (or A in the complementary strand) |
| $X_{10}$ | G | A or G | May have G (or C in the complementary strand) but not A (or C in the complementary strand) |
| $X_{11}$ | C | T | May have C (or G in the complementary strand), but not T (or A in the complementary strand) |
| $X_{12}$ | T | C | May have T (or A in the complementary strand), but not C (or G in the complementary strand) |
| $X_{13}$ | A or T | T | |
| $X_{14}$ | A or C | C | (EV amplicons will not have A (or T in the complementary strand)) |

-continued

| Nucleotide | In HRV isolates (SEQ ID NO: 4), this residue is | In EV isolates (SEQ ID NO: 5), this residue is | An amplified product from HRV (or, shown in parentheses, an amplified product from EV) |
|---|---|---|---|
| $X_{15}$ | C | C or T | May have C (or G in the complementary strand) but not T (or A in the complementary strand) |
| $X_{16}$ | C | A or G | May have C (or G in the complementary strand) but not A (or T in the complementary strand) |
| $X_{17}$ | C or T | C | (EV amplicons will not have T (or A in the complementary strand)) |
| $X_{18}$ | A or G | G | (EV amplicons will not have A (or T in the complementary strand)) |
| $X_{19}$ | C or G | G | |

Thus in one embodiment, detection of different HRV serotypes so as to exclude EV detects a target sequence of

```
                                   (SEQ ID NO:6 and 11)
GGTGX₁GAAGA X₂X₃CX₄X₅X₆TGX₇G CTCACTTNT X₈X₉A

X₁₀TCCTCCGG CCCCTGAATG CGGCTAAX₁₁CX₁₂ X₁₃AAX₁₄

X₁₅X₁₆X₁₇ X₁₈X₁₉A GC
or a complement thereof,
``` where $X_1$ is not C, $X_2$ is G or C, $X_3$ is C or T, $X_4$ is A, C or G, $X_5$ is not A, $X_6$ is not T, $X_7$ is T, $X_8$ is not G, $X_9$ is not T, $X_{10}$ is not A, $X_{11}$ is not T, $X_{12}$ is not C, $X_{13}$ is A or T, $X_{14}$ is A or C, $X_{15}$ is not T, $X_{16}$ is not A, $X_{17}$ is C or T, X is A or G, and $X_{19}$ is C or G.

Alternatively or in addition, detection of different HRV serotypes so as to exclude EV detects this target sequence where $X_1$ is T, $X_2$ is G or C, $X_3$ is C or T, $X_4$ is A, C or G, $X_5$ is C, $X_6$ is G or A, $X_7$ is T, $X_8$ is T, $X_9$ is G, $X_{10}$ is G, $X_{11}$ is C, $X_{12}$ is T, $X_{13}$ is A or T, $X_{14}$ is A or C, $X_{15}$ is C, $X_{16}$ is C, $X_{17}$ is C or T, $X_{18}$ is A or G, and $X_{19}$ is C or G.

HRV target sequences in amplification products can also be distinguished from EV-derived amplification products by noting that in the corresponding EV sequence $X_3$ is not T, $X_4$ is not C or G, $X_{14}$ is not A, $X_{17}$ is not T, and $X_{18}$ is not A, in either the target sequence or in the corresponding residue in the complementary strand.

Specific detection of HRV (e.g., so as to avoid a false positive result due to detection of EV) can be avoided by providing for detection of all or a portion of the target sequence having a sequence that allows for discrimination between HRV and EV. For example, because HRV and EV can have the same nucleotide at positions $X_1$, $X_2$, $X_3$, $X_9$, $X_{10}$, $X_{13}$, $X_{14}$, $X_{15}$, $X_{17}$, $X_{18}$, and/or $X_{19}$ of the consensus sequence provided above, these nucleotides can not be used to discriminate between an HRV isolate and an EV isolate. However, one or more of nucleotides $X_4$, $X_5$, $X_6$, $X_7$, $X_8$, $X_{11}$, $X_{12}$, and $X_{16}$ of the consensus sequence can be used to (distinguish an HRV isolate from an EV isolate. Thus in one embodiment, the assay provides for specific detection of HRV where the nucleotide at 1, 2, 3, 4, 5, 6, 7 or all 8 of the positions $X_4$, $X_6$, $X_7$, $X_8$, $X_{11}$, $X_{12}$, and $X_{16}$ of the consensus target sequence have a nucleotide at that position indicative of an HRV isolate (e.g., $X_4$ is not T, $X_5$ is not A, $X_6$ is not T, $X_7$ is not A, $X_8$ is not R (A or G), $X_{11}$ is not T, $X_{12}$ is not C, and $X_{16}$ is not R (A or G)).

In another embodiment, the assay provides for detection of HRV based on detection of portions of the target sequence discussed above. This embodiment is based on the observation that, as exemplified below, the nucleotide sequence of the regions of the consensus sequence between the sequences against which primers and probes are designed are not important for specific detection of HRV. Stated differently, the portion of the consensus sequence between the 5' primer and the probe (i.e., the sequence 3' of the 5'primer and 5' of the probe) and between the probe and the 3' primer (i.e., the sequence 5' of the probe and 3' of the 3' primer) are not critical to detection of HRV according to the invention using, for example, a nucleic acid-based amplification assay. Thus, in this embodiment, the target consensus sequence for nucleic acid-based amplification is:

```
                                   (SEQ ID NO:7 and 12)
GGTGX₁GAAGA X₂X₃CX₄X₅X₆TGX₇G CTNNNNNNN X₈X₉A

X₁₀TCCTCCGG CCCCTGAATG NGGCTAAX₁₁CX₁₂ X₁₃AAX₁₄

X₁₅X₁₆X₁₇ X₁₈X₁₉A GC
or a complement thererof,
``` where N is any nucleotide, and where HRV nucleic acid is detected when $X_1$ is not C, $X_2$ is G or C, $X_3$ is C or T, is A, C or G, $X_5$ is not A, $X_6$ is not T, $X_7$ is T, $X_8$ is not G, $X_9$ is not T, $X_{10}$ is not A, $X_{11}$ is not T, $X_{12}$ is not C, $X_{13}$ is A or T, $X_{14}$ is A or C, $X_{15}$ is not T, $X_{16}$ is not A, $X_{17}$ is C or T, $X_{18}$ is A or G, and $X_{19}$ is C or G. Alternatively or in addition, detection of different HRV serotypes so as to exclude EV detects this target sequence where $X_1$ is T, $X_2$ is G or C, $X_3$ is C or T, $X_4$ is A, C or G, $X_5$ is C, $X_6$ is G or A, $X_7$ is T, $X_8$ is T, $X_9$ is G, $X_{10}$ is G, $X_{11}$ is C, $X_{12}$ is T, $X_{13}$ is A or T, $X_{14}$ is A or C, $X_{15}$ is C, $X_{16}$ is C, $X_{17}$ is C or T, $X_{18}$ is A or G, and $X_{19}$ is C or G.

In one embodiment, detection of HRV nucleic acid using nucleic acid-based amplification involves detection of an target nucleic acid as amplification product having three target sequence regions, or their complements, as follows:

```
Target Sequence Region 1:
                                   (SEQ ID NO:8 and 13)
GGTGX₁GAAGA X₂X₃CX₄X₅X₆TGX₇G CT Target Sequence Region 2:
                                   (SEQ ID NO:9 and 14)
GGCTAAX₁₁CX₁₂ X₁₃AAX₁₄ X₁₅X₁₆X₁₇ X₁₈X₁₉A GC Target Sequence Region 3:
                                   (SEQ ID NO:10 and 15)
X₈X₉A X₁₀TCCTCCGG CCCCTGAATG
``` where the nucleotides $X_1$-$X_{19}$ can be defined as set out above. Specifically, in each of the target sequence regions, HRV nucleic acid is detected when $X_1$ is not C, $X_2$ is G or C, $X_3$ is C or T, is A, C or G, $X_5$ is not A, $X_6$ is not T, $X_7$ is T, $X_8$ is not G, $X_9$ is not T, $X_{10}$ is not A, $X_{11}$ is not T, $X_{12}$ is not C, $X_{13}$ is A or T, $X_{14}$ is A or C, $X_{15}$ is not T, $X_{16}$ is not A, $X_{17}$ is C or T, $X_{18}$ is A or G, and $X_{19}$ is C or G. Alternatively or in addition, detection of different HRV serotypes so as to exclude EV detects this target sequence where $X_1$ is T, $X_2$ is G or C, $X_3$ is C or T, $X_4$ is A, C or G, $X_5$ is C, $X_6$ is G or A, $X_7$ is T, $X_8$ is T, $X_9$ is G, $X_{10}$ is G, $X_{11}$ is C, $X_{12}$ is T, $X_{13}$ is A or T, $X_{14}$ is A or C, $X_{15}$ is C, $X_{16}$ is C, $X_{17}$ is C or T, $X_{18}$ is A or G, and $X_{19}$ is C or G.

In one embodiment, HRV target nucleic acid is detected by use of primers designed from the sequences of target sequence regions 1 and 2, and, preferably, a probe designed from the sequence of target sequence region 3, where target sequence regions 1, 2 and 3 appear in the target sequence exemplified in FIG. 1 in the order, from 5 to 3' or 1, 3, and 2.

The assay contemplates detection of a target nucleic acid having a target sequence described herein, where the target nucleic acid can be of any length. Preferably, the target nucleic acid is detected as a nucleic acid of less than about 500, 400, 300, 250, 200, 180, 175, 170, 165, 160, 155, 150, 145, 140, 135, 130, 125, 120, 115, 110, 105, 100, 95, 90, 85, 80, 79, 78, 77, 76, 75, 74, or 73 nucleotides in length, with detection of a target nucleic acid of less than about 100, 95, 90, 85, 80, 79, 78, 77, 76, 75, 74, or 73 nucleotides in length and comprising the target sequence being preferred in the context of nucleic acid-based amplification assays.

Detection of an HRV nucleic acid is confirmed when the nucleic acid in the sample comprises a sequence that is at least 85%, 89%, 90%, 91%, 92%, 93%, 94%, 95%, 96%, 97%, 98%, or 99% or more identical in sequence to the target sequence of 72 nucleotide residues described above. Based on the observation that in the nucleic acid-based amplification assays of the working examples below, detection of sequence between the sequences corresponding to the primers and probes (a total of eight residues) was not important to the desirable characteristics of the assay, thus indicating that the target sequence can vary by about 11% in sequence overall taking these intervening regions into account.

An exemplary target sequence based on the sequence from at least 17 different HRV serotypes representative of different subgroups, is shown in FIG. 1. When the genomic sequences of the target sequence of these serotypes is compared, 61 of the 72 nucleotide residue positions of the target sequence are conserved among the isolates analyzed, where variant nucleotides as well as deletions and insertions are taken into account (see FIGS. 3A-3D). This observation indicates that of the isolates examined, the target sequence displays at least about 84.7%, about 85%, about 87%, about 90%, about 95%, about 97%, about 98%, about 99% or more sequence identity from isolate to isolate. Of the sequence differences, two are insertions/deletions that occur outside of target sequence regions 1, 2 and 3 (which correspond to the 5' primer, probe, and 3' primer, respectively, in FIG. 1).

Of the nucleotide residues of target sequence region 1 (shown in FIG. 1 as corresponding to a 5' primer), 18 of 22 are conserved among the isolates analyzed, with no insertions or deletions of residues being observed, indicating that target sequence region 1 is at least about 81%, about 82%, about 85%, about 87%, about 90%, about 95%, about 97%, about 98%, about 99% or more identical in sequence from isolate to isolate. Of these 22 nucleotides, in some embodiments only one residue of the sequence, indicated as Y (C or T) in FIG. 1, may be identical to the residue at the corresponding position in EV.

Of the nucleotide residues of target sequence region 2 (shown in FIG. 1 as corresponding to a 3' primer), 16 of 21 are conserved among the isolates analyzed, with no insertions or deletions of residues being observed, indicating that target sequence region 2 is at least about 76%, 80% 81%, about 82%, about 85%, about 87%, about 90%, about 95%, about 97%, about 98%, about 99% or more identical in sequence from isolate to isolate. Of these 21 nucleotides of target sequence region 2, one residue may be identical to the residue at the corresponding position in EV.

Of the nucleotide residues of target sequence region 3 (shown in FIG. 1 as corresponding to a probe), no variants were identified among the HRV isolates analyzed, with no insertions or deletions of residues being observed. Of the 22 nucleotides of target sequence region 3, two of the residues may be identical to the residue at the corresponding position in EV.

The target nucleic acid, as well as fragments thereof which are characterized as regions of interest for primers and probes, are readily obtained from additional isolates using portions of the HRV sequence as described herein, e.g. by PCR amplification or through analysis of sequences of HRV available in public data bases and the like.

Nucleic acid having the desired sequences can also be obtained by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) Proc. Natl. Acad. Sci. USA 88:4084-4088. Once the sequences have been prepared or isolated, they can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements. Recombinant clones are readily identified by restriction enzyme analysis and polyacryamide or agarose gel electrophresis, using techniques well known in the art, and described in the examples below.

In view of the above, it will be apparent to the ordinarily skilled artisan upon reading the specification that the assays of the invention can be designed in a variety of ways to detect the target nucleic acid and determine the presence or absence of HRV nucleic acid in a sample having or suspect of having HRV nucleic acid. Preferably, and where desired, the assay can provide for specific detection of HRV in a manner that reduces the probability of false positives that can result from detection of a picornavirus, particularly due to detection of EV nucleic acid.

Primers and Probes

As described above, a target nucleic acid sequence region that is highly conserved across many HRV serotypes representative of different HRV subgroups is found within a region of about 100 nucleotides, more specifically about 75 nucleotides, even more specifically 72 nucleotides, within the 5'UTR of HRV. Primers and probes for use in these assays are preferably derived from the target sequence within the 5' UTR of HRV as described above. Particularly preferred primers and probes for use with the present assays are designed from highly conserved regions of the HRV 5'UTR to allow detection of HRV from a variety of isolates, preferably while avoiding detection of and/or allowing discrimination from non-HRV viruses, such as EV.

In an embodiment of particular interest, the assay is an amplification-based assay using degenerate primers and probes, where the primers and probes are designed to provide for amplification of HRV having different nucleic acid sequences, while avoiding amplification of a detectable or a significant amount of a non-HRV picornaviral nucleic acid, particularly EV, thus allowing for detection of different rhinovirus with different target nucleic acid sequences while not substantially compromising the assay's feature in avoiding false negatives.

As discussed above, in one embodiment, the primers and/or probes are designed for nucleic acid-based detection, particularly an amplification method, of a target nucleic acid having a target consensus sequence of

```
                                       (SEQ ID NO:7 and 12)
GGTGX₁GAAGA  X₂X₃CX₄X₅X₆TGX₇G  CTNNNNNNNN  X₈X₉A

X₁₀TCCTCCGG  CCCCTGAATG  NGGCTAAX₁₁CX₁₂  X₁₃AAX₁₄

X₁₅X₁₆X₁₇  X₁₈X₁₉A  GC
or a complement thereof,
``` where N is any nucleotide, and where HRV nucleic acid is detected when $X_1$ is not C, $X_2$ is G or C, $X_3$ is C or T, is A, C or G, $X_5$ is not A, $X_6$ is not T, $X_7$ is T, $X_8$ is not G, $X_9$ is not T, $X_{10}$ is not A, $X_1$ is not T, $X_{12}$ is not C, $X_{13}$ is A or T, $X_{14}$ is A or C, $X_{15}$ is not T, $X_{16}$ is not A, $X_{17}$ is C or T, $X_{18}$ is A or G, and $X_{19}$ is C or G. Alternatively or in addition, detection of different HRV serotypes so as to exclude EV detects this target sequence where $X_1$ is T, $X_2$ is G or C, $X_3$ is C or T, $X_4$ is A, C or G, $X_5$ is C, $X_6$ is G or A, $X_7$ is T, $X_8$ is T, $X_9$ is G, $X_{10}$ is G, $X_{11}$ is C, $X_{12}$ is T, $X_{13}$ is A or T, $X_{14}$ is A or C, $X_{15}$ is C, $X_{16}$ is C, $X_{17}$ is C or T, $X_{18}$ is A or G, and $X_{19}$ is C or G.

In one embodiment, primers and/or probes are designed for detection of HRV nucleic acid using nucleic acid-based detection particularly an amplification method, of an target nucleic acid as amplification product having three target sequence regions as follows:

```
Target Sequence Region 1:
                                       (SEQ ID NO:8 and 13)
GGTGX₁GAAGA  X₂X₃CX₄X₅X₆TGX₇G  CT Target Sequence Region 2:
                                       (SEQ ID NO:9 and 14)
GGCTAAX₁₁CX₁₂  X₁₃AAX₁₄  X₁₅X₁₆X₁₇  X₁₈X₁₉A  GC Target Sequence Region 3:
                                       (SEQ ID NO:10 and 15)
X₈X₉A  X₁₀TCCTCCGG  CCCCTGAATG
``` where the nucleotides $X_1$-$X_{19}$ can be defined as set out above. Specifically, in each of the target sequence regions, HRV nucleic acid is detected when $X_1$ is not C, $X_2$ is G or C, $X_3$ is C or T, $X_4$ is A, C or G, $X_5$ is not A, $X_6$ is not T, $X_7$ is T, $X_8$ is not G, $X_9$ is not T, $X_{10}$ is not A, $X_{11}$ is not T, $X_{12}$ is not C, $X_{13}$ is A or T, $X_{14}$ is A or C, $X_{15}$ is not T, $X_{16}$ is not A, $X_{17}$ is C or T, $X_{18}$ is A or G, and $X_{19}$ is C or G. Alternatively or in addition, detection of different HRV serotypes so as to exclude EV detects this target sequence where $X_1$ is T, $X_2$ is G or C, $X_3$ is C or T, $X_4$ is A, C or G, $X_5$ is C, $X_6$ is G or A, $X_7$ is T, $X_8$ is T, $X_9$ is G, $X_{10}$ is G, $X_{11}$ is C, $X_2$ is T, $X_{13}$ is A or T, $X_{14}$ is A or C, $X_{15}$ is C, $X_{16}$ is C, $X_{17}$ is C or T, $X_{18}$ is A or G, and $X_{19}$ is C or G.

Specific detection of HRV nucleic acid is generally accomplished by detection of all three target sequence regions. In one embodiment, HRV target nucleic acid is detected by use of primers and probes designed upon the sequences of target sequence regions 1, 2, and 3, respectively.

In an embodiment of particular interest, the target sequence is detected using primers having the sequence GGTGTGAAGASYCVCRTGTGCT (5' primer) (SEQ ID NO: 16) and GCTSYRGGKTTWAGGTTAGCC (3' primer) (SEQ ID NO: 17), and a probe having the sequence TGAGTCCTCCGGC-CCCTGAATG (SEQ ID NO: 18) is of particular interest. Of particular interest is the use of these primers and probes in a real-time RT PCR method for detection of HRV, with use of a dual-labeled TaqMan Probe.

In general, the primers provide for amplification of target nucleic acid to produce as target nucleic acid amplification product (an "amplicon").

Primers may be, and preferably are, used in connection with a probe. 5' primers generally bind to a region to provide for amplification of the target nucleic, and preferably bind to a 5' portion of the target sequence, as exemplified in FIG. 1. 3' primers generally bind to a sequence that is complementary to a 3' portion of the nucleic acid generated by extension from the 5' primer, as exemplified in FIG. 1. The 5' and 3' primers may be separated by about 10, 20, 30, or 40 contiguous nucleotides, usually about 30 contiguous nucleotides.

Primers and probes for use in the assays herein are designed based on the sequence disclosed herein and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly (A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

Typically, the primer sequences are in the range of between 10-75 nucleotides in length, such as 10 to 70, 12 to 65, 15 to 60, 20 to 55, 25 to 50, 30 to 45, and the like. More typically, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides in length are of particular interest.

The typical probe is in the range of between 10-50 nucleotides long, such as 10 to 50, 12 to 45, 15 to 40, 20 to 35, 25 to 30 and the like. More typically, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides in length are of particular interest.

The probes may be coupled with labels for detection. There are several methods and compositions known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Preferred fluorescent labels include fluorescein and derivatives thereof, such as disclosed in U.S. Pat. No. 4,318, 846 and Lee et al., Cytometry (1989) 10:151-164, and 6-FAM, JOE, TAMRA, ROX, HEX-1, HEX-2, ZOE, TET-1 or NAN-2, and the like.

Additionally probes can be labeled with an acridinium ester (AE). Current technologies allow the AE label to be placed at any location within the probe. See, e.g., Nelson et al (1995) "Detection of Acridinium Esters by Chemiluminescence" in Nonisotopic Probing Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

If a solid support is used in the assay (e.g., to capture amplicons of target nucleic acid using a probe), the oligonucleotide probe may be attached to the solid support in a variety of manners. For example, the probe may be attached to the solid support by attachment of the 3' or 5' terminal nucleotide of the probe to the solid support. More preferably, the probe is attached to the solid support by a linker which serves to distance the probe from the solid support. The linker is usually at least 15-30 atoms in length, more preferably at least 15-50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred.

The linkages between the solid support, the linker and the probe are normally not cleaved during removal of base protecting groups under basic conditions at high temperature. Examples of preferred linkages include carbamate and amide linkages.

Examples of preferred types of solid supports for immobilization of the oligonucleotide probe include controlled pore glass, glass plates, polystyrene, avidin-coated polystyrene beads, cellulose, nylon, acrylamide gel and activated dextran.

In certain embodiments, an internal control (IC) or an internal standard is added to serve as a control to show that any negative result is not due to failure of the assay. The use of the IC permits the control of the extraction process, the amplification process, and the detection system, and permits the monitoring of assay performance and quantification for the sample(s). The IC can be included at any suitable point, for example, in the lysis buffer. In one embodiment, the IC comprises phage nucleic acid. Where a solid support is used in the assay, the solid support may additionally include probes specific to the internal standard (IC probe), thereby facilitating capture when using the IC probe, The IC probe can optionally be coupled with a detectable label that is different from the detectable label for the target sequence. In embodiments where the detectable label is a fluorophore, the IC can be quantified spectrophotometrically and by limit of detection studies.

In another embodiment, an IC, as described herein, is combined with RNA isolated from the sample according to standard techniques known to those of skill in the art, and described herein. The RNA is then reverse-transcribed using a reverse transcriptase to provide copy DNA. The cDNA sequences can be optionally amplified (e.g., by PCR) using labeled primers. The amplification products are separated, typically by electrophoresis, and the amount of radioactivity (proportional to the amount of amplified product) is determined. The amount of mRNA in the sample can then calculated where desired by comparison with the signal produced by the known standards.

Methods of Detection

The invention provides DNA-based assay for detecting HRV in a sample. In preferred embodiments, the methods discriminate between HRV and EVs, and other phylogenetically related members of Picornavircidae. Detection may be done using a wide variety of methods, including direct sequencing, hybridization with sequence-specific oligomers, gel electrophoresis and mass spectrometry. These methods can use heterogeneous or homogeneous formats, isotopic or nonisotopic labels, as well as no labels at all.

Preferably, the method involves amplifying nucleic acids from a sample, which amplifying step follows a reverse transcription step to provide a cDNA template for amplification. If a diagnostic nucleic acid is obtained, the presence of HRV in a sample is indicated. In general, the methods involve amplifying a nucleic acid from a sample using a primer and at least one other primer, as described above, and assessing the amplified nucleic acids. The methods are highly sensitive, and may detect as few as 200 copies of HRV ($9 \times 10^3$ copies/ml), although limit of linear range detection ends at $2 \times 10^4$ copies of RNA, which is equivalent to $9 \times 10^3$ copies of RNA per mL of specimen. Thus, the invention generally provides for detection of HRV in a sample, where the HRV is present in at least $9 \times 10^3$ copies of RNA per mL of specimen.

As is known in the art, an amplified nucleic acid may be assessed by a number of methods, including, for example, determining the presence or absence of the nucleic acid, determining the size of the nucleic acid or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

For example, primers and probes described above may be used in polymerase chain reaction (PCR)-based techniques to detect HRV in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g. Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324: 163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers which are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands.

The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer.

RNAs of HRV can be amplified by reverse transcribing the mRNA into cDNA, and then performing PCR (RT-PCR), as described above. Alternatively, a single enzyme may be used for both steps as described in U.S. Pat. No. 5,322,770. mRNA may also be reverse transcribed into cDNA, followed by asymmetric gap ligase chain reaction (RT-AGLCR) as described by Marshall et al. (1994) PCR Meth. App. 4:80-84.

The fluorogenic 5' nuclease assay, known as the TAQ-MAN™ assay (Perkin-Elmer), is a powerful and versatile PCR-based detection system for nucleic acid targets. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes derived from regions of the HRV genome described herein can be used in TAQMAN™ analyses to detect the presence of infection in a biological sample. Analysis is performed in conjunction with thermal cycling by monitoring the generation of fluorescence signals. The assay system dispenses with the need for gel electrophoretic analysis, and has the capability to generate quantitative data allowing the determination of target copy numbers.

The fluorogenic 5' nuclease assay is conveniently performed using, for example, AMPLITAQ GOLD DNA polymerase, which has endogenous 5' nuclease activity, to digest an internal oligonucleotide probe labeled with both a fluorescent reporter dye and a quencher (see, Holland et al., Proc. Natl. Acad. Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, the present invention relates to methods for amplifying a target HRV nucleotide sequence using a nucleic acid polymerase having 5' to 3' nuclease activity, one or more primers capable of hybridizing to the target HRV sequence or its extension product, and an oligonucleotide probe capable of hybridizing to the target HRV sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is preferably a fluorescein dye and the quencher molecule is preferably a rhodamine dye.

The HRV sequences described herein may also be used as a basis for transcription-mediated amplification (TMA) assays. TMA provides a method of identifying target nucleic acid sequences present in very small amounts in a biological sample. Such sequences may be difficult or impossible to detect using direct assay methods. In particular, TMA is an isothermal, autocatalytic nucleic acid target amplification system that can provide more than a billion RNA copies of a target sequence. The assay can be done qualitatively, to accurately detect the presence or absence of the target sequence in a biological sample. The assay can also provide a quantitative measure of the amount of target sequence over a concentration range of several orders of magnitude. TMA provides a method for autocatalytically synthesizing multiple copies of a target nucleic acid sequence without repetitive manipulation of reaction conditions such as temperature, ionic strength and pH.

Generally, TMA includes the following steps: (a) isolating nucleic acid from the biological sample of interest suspected of having HRV; and (b) combining into a reaction mixture (i) the isolated nucleic acid, (ii) first and second oligonucleotide primers, the first primer having a complexing sequence sufficiently complementary to the 3' terminal portion of an RNA target sequence, if present (for example the (+) strand), to complex therewith, and the second primer having a complexing sequence sufficiently complementary to the 3' terminal portion of the target sequence of its complement (for example, the (−) strand) to complex therewith, wherein the first oligonucleotide further comprises a sequence 5' to the complexing sequence which includes a promoter, (iii) a reverse transcriptase or RNA and DNA dependent DNA polymerases, (iv) an enzyme activity which selectively degrades the RNA strand of an RNA-DNA complex (such as an RNAse H) and (v) an RNA polymerase which recognizes the promoter.

The components of the reaction mixture may be combined stepwise or at once. The reaction mixture is incubated under conditions whereby an oligonucleotide/target sequence is formed, including DNA priming and nucleic acid synthesizing conditions (including ribonucleotide triphosphates and deoxyribonucleotide triphosphates) for a period of time sufficient to provide multiple copies of the target sequence. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH. The reaction conveniently does not require a denaturation step to separate the RNA-DNA complex produced by the first DNA extension reaction.

Suitable DNA polymeraes include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. It may, however, be preferable to add exogenous RNAse H, such as *E. coli* RNAse H, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Another method of detection involves use of target sequence-specific oligonucleotide probes, which contain a region of complementarity to the target sequence described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70 degrees celsius. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

TMA is described in detail in, e.g., U.S. Pat. No. 5,399,491, the disclosure of which is incorporated herein by reference in its entirety. In one example of a typical assay, an isolated nucleic acid sample, suspected of containing HRV, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

The oligonucleotide molecules of the present invention may also be used in nucleic acid sequence-based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTP's and dNTP's. Using NASBA, large amounts of single-stranded RNA are generated from either single-stranded RNA or DNA, or double-stranded DNA. When RNA is to be amplified, the ssRNA serves as a template for the synthesis of a first DNA strand by elongation of a first primer containing an RNA polymerase recognition site. This DNA strand in turn serves as the template for the synthesis of a second, complementary, DNA strand by elongation of a second primer, resulting in a double-stranded active RNA-polymerase promoter site, and the second DNA strand serves as a template for the synthesis of large amounts of the first template, the ssRNA, with the aid of a RNA polymerase. The NASBA technique is known in the art and described in, e.g., European Patent 329,822, International Patent Application No. WO 91/02814, and U.S. Pat. Nos. 6,063,603, 5,554,517 and 5,409,818, all of which are incorporated herein in their entireties.

The HRV sequences described herein are also useful in nucleic acid hybridization and amplification techniques that utilize branched DNA molecules. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal uses amplification multimers that are polynucleotides with a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are useful in these techniques: forked and combed. Methods for making and using branched nucleic acid molecules are known in the art and described in, e.g., U.S. Pat. No. 5,849,481, incorporated herein by reference in its entirety.

As is readily apparent, design of the assays described herein are subject to a great deal of variation, and many formats are known in the art. The above descriptions are merely provided as guidance and one of skill in the art can readily modify the described protocols, using techniques well known in the art.

Kits

Kits for use in connection with the subject invention are also provided. The above-described assay reagents, including the primers, probes, solid support with bound probes, as well as other detection reagents, can be provided in kits, with suitable instructions and other necessary reagents, in order to conduct the assays as described above. The kit will normally contain in separate containers the combination of primers and probes (either already bound to a solid matrix or separate with reagents for binding them to the matrix), control formulations (positive and/or negative), labeled reagents when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In general, kits of the invention include at least one primer, usually at least two primers (a 5' and a 3' primer), usually at least two primers and a probe, as described above. Kits may also contain instructions for using the kit to detect HRV in a sample using the methods described above, including the above discussed PCR methods. Also included in the subject kits may be buffers, dNTPs, and controls, (e.g., positive and negative control nucleic acids) for performing the subject methods. Primers in the subject kits may be detectably labeled or unlabeled).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials were used in the Example(s) below.

Specimen types and handling. Samples for use in detection of HRV according to the invention can be any suitable biological sample, usually samples taken from the respiratory tract. Nasopharyngeal aspirates (NPA) (0.5 mL) should be collected in sterile, leak-proof container and, if need, shipped on dry ice via overnight express. Bronchial washing, bronchoalveolar lavage (BAL) (~2 mLs) should be collected in a sterile, leak-proof container and shipped frozen via overnight express. Swab specimens should be placed in transport medium, stored frozen at −20±10° C. and as needed shipped on dry ice via overnight express. All of the above specimen types can be stable frozen at −70° C.($\leq$−60° C.) for 6 months prior to analysis. Samples not processed upon arrival at the site where analysis is to be performed should be maintained fresh at −20±10° C., if they are not to be processed upon arrival.

Enzymes. The following enzymes are used: 2× TaqMan® Universal PCR Master Mix Applied Biosystems Cat. #4304437 or 4318157; M-MuLV Reverse Transcriptase (supplied with a 10×RT Buffer); and RNAsin Ribonuclease Inhibitor.

Primers and Probes. Primers and fluorogenic probes were synthesized by qualified vendors. Oligonucleotide primers were desalted and lyophilized. Degenerate primers for detection of HRV were as follows (10 µM working concentration):

```
HRV-F1:
                                  (SEQ ID NO:16)
5'-GGT GTG AAG ASY CVC RTG TGC T-3'

HRV-R1:
                                  (SEQ ID NO:17)
5'-GCT SYR GGK TTW AGG TTA GCC-3'
``` where: S=C or G; Y=C or T; V=A, C, or G; R=A or G; K=G or T; and W=A or T. "F" refers to the forward primer; "R" to the reverse primer. The probe used in connection with these primers was:

```
HRV-TM1
                                  (SEQ ID NO:18)
6FAM-TGA GTC CTC CGG CCC CTG AAT G-TAMRA
```

Probes are frozen at a 100 µM concentration. The working concentration of HRV-TM1 is 10 µM, and is diluted 1:10 with 10 mM Tris-HCl, pH 8.0, and distributed into 100 µL aliquots. Probes can be stored at −10° C. or lower and protected from light.

Primers for MS2 RNA (at 10 µM working concentration) were:

```
BS3:
                                  (SEQ ID NO:19)
5'-AAC GAG ACC TTC GTC CCC TC-3'

BS4:
                                  (SEQ ID NO:20)
5'-TTA ACG CCC CCC GTG AAT ACG-3'
```

HRV and MS2 primers were prepared by briefly centrifuging the tubes containing lyophilized primer before opening tube, and adding an equal volume-to-weight amount of RNAse-free water to each primer tube. Primers were incubated at 20°-25° C. for 1 to 2 hours to dissolve, vortexing every 30 minutes (approximately). 3 µL of dissolved primer was transferred into a clean microcentrifuge tube containing 147 µL of RNAse free water for a 1:50 dilution, then incubates at 20°-25° C. 30 minutes, minimum, with vortexing every 10-15 minutes. The concentration of primer (µg/L) of the primers was then determined, and the molar concentration of the primers determined based on the molecular weight, where the molecular weights of the probes were as follows: HRV-F1: 6808 g/mol; HRV-R1: 6481 g/mol; BS3: 6600 g/mol; and BS4: 6930 g/mol. Primers were then diluted to the appropriate working concentration of 10 µM using RNAse-free water.

HRV Positive Control. RNA extracted from cell culture of Serotype 16 strain of HRV was used as the positive control for HRV real-time RT-PCR. A positive control, HRV PC, is made to have a $C_T$ value, when amplified and detected as described below, of 30-34. The $C_T$ value (or "cycle threshold") is the number of the PCR cycle at which a statistically significant increase in reporter fluorescence can be detected above the baseline. The RNA used as positive control was allocated into 1.5 mL flip-cap tubes and was frozen at −10° C. or lower in 25-50 µL volumes.

Reagents and Buffers. The following were used in the assays: QIAamp Viral RNA Mini Kit 250 Test (QIAGEN Cat. #51106); MS2 RNA (Roche Molecular Cat. #165 948) (diluted to 10 pg/µL with RNAse-free water); Absolute Ethyl Alcohol; 70% ethyl alcohol; RNAse-free water; DNA Loading Buffer (Glycerol 50% w/v (0.50 mL), 25 mM EDTA pH 7.4 (0.25 mL), Xylene Cyanol (5 mg), Bromophenol Blue (5 mg), and Sterile H$_2$O (1.25 mL)), 5×TBE Buffer (0.9 M Trizma Base (218.0 g), 0.9 M Boric Acid (110.0 g), 25 mM EDTA (18.8 g) and dH$_2$O to four liters pH 8.3), and Ethidium Bromide.

dNTP Solution was made of individual nucleotide triphosphate solutions supplied at a 100 mM concentration. The working concentration of dNTP solution was 2.5 mM and reconstituted as follows:

| | |
|---|---|
| dATP (100 mM) | 250 µL |
| dCTP (100 mM) | 250 µL |
| dGTP (100 mM) | 250 µL |
| dTTP (100 mM) | 250 µL |
| H$_2$O | 9 mL |

Equipment. Equipment used included the following: Perkin Elmer 9600 or 9700 Thermocycler; Perkin Elmer Cetus DNA Thermocycler, and the ABI PRISM® Sequence Detection System.

Quality control measures. For Extraction Control, RNAse free water was used in place of clinical specimen for an extraction negative control. In addition, MS2 phage was used as an extraction internal control. Each specimen, at the time of sample processing, was spiked with 50 pg MS2 phage RNA (5 µL of 10 pg/µL). The processed sample was then subjected to RT-PCR using primers BS3/BS4 which are specific for sequences on the MS2 RNA. Successful amplification yields a 166 bp product, which can be seen on a 2% agarose gel. Failure to yield the 166 bp product suggests that either RNA extraction from the sample was unsuccessful or that inhibitory substances were in the processed sample.

For RT-PCR a water control was used for each RT-PCR run as a negative control, with RNAse free water added to the master mix aliquot instead of RNA. The HRV positive control described above was included in each RT-PCR run.

To minimize potential cross-contamination, reagent preparation, specimen processing, RT-PCR set up; amplification and gel electrophoresis are each carried out in physically separated laboratories with instrumentation dedicated to each separate step.

Procedure for Sample Processing. QIAGEN AVL buffer was prepared by adding 1 mL of AVL Lysis buffer is added to one tube of lyophilized Carrier RNA and the Carrier RNA dissolved thoroughly, the solution transferred back into the AVL buffer bottle, and mixed well Buffer AW1 was prepared by adding the appropriate amount of absolute ethanol (200 proof) to Buffer AW1 concentrate as indicated on the bottle. For the 50 and 250 preparation kits, 25 mL and 125 mL of absolute ethanol was added respectively. Final buffer volumes were 44 mL and 220 mL, for the 50, and 250 preparation kits respectively. Buffer AW2 was prepared by adding the appropriate amount of absolute ethanol (200 proof) to Buffer AW2 concentrate as indicated on the bottle. For the 50 and 250 preparation kits, 30 mL and 160 mL of absolute ethanol were added, respectively. Final buffer volumes were 43 mL and 226 mL, for the 50, and 250 preparation kits respectively.

All samples were brought to 20-25° C. A 1.5 mL tube of RNAse-free dH$_2$O was placed in the 60° C.±3° C. heat block. Patient specimen were vortexed for 5-10 seconds. After adding 560 µL of buffer AVL containing Carrier RNA into a 1.5 mL microcentrifuge tube, 140 µL of patient specimen was added to the tube, followed by 5 µL of MS2 (10 pg/µL). The tube was capped and vortexed for 5-10 seconds, incubated at 20-25° C. for 10 minutes, then centrifuged to collect droplets inside the lid. 560 µL of absolute ethyl alcohol was added, the tube capped and vortexed for 5-10 seconds, then briefly centrifuged to collect droplets inside the lid. Nucleic acid is then isolated from this sample mixture using a QIAamp spin column.

Briefly, a QIAamp spin column was placed in a 2-mL collection tube, and the mixture from the tube carefully applies to the QIAamp spin column without moistening the rim or touching the white membrane. The tube was then capped, and centrifuges at 6000×g (8200 rpm) for 1 minute at 20-25° C. After centrifugation, the QIAamp spin column is placed in a clean 2-mL collection tube, and the tube containing the filtrate discarded. This step is repeated until the sample mixture from above has all been run through the spin column.

500 µL of Buffer AW1 I is then added to each column, using a separate pipet tip for each sample, and centrifuged at 6000×g (8200 rpm) for 1 minute at 20-25° C. After centrifugation, the QIAamp spin column is plaed in a clean 2-mL collection tube, and the collection tube containing the filtrate discarded. 500 µL of Buffer AW2 is then added to each column using a separate pipette for each column, then the column centrifuged at full speed (≧13,000 rpm) for 3 minutes at 20-25° C. The spin column was then placed in a clean 2-mL collection tube, and the collection tube containing the filtrate discarded. The spin column was then centrifuged at full speed (≧13,000 rpm) for 1 minute at 20-25° C. to remove any residual filtrate.

The QIAamp spin column is then placed in a clean 1.5-mL microcentrifuge tube, and the collection tube containing the filtrate discarded. The cap of the column is opened for about 5-10 minutes to allow evaporation of any remaining ethanol in the column. 60 µL of preheated RNAse-free dH$_2$O is added, incubated at 2025° C. for 1 minute, and then centrifuged at 6000×g (8200 rpm) for 1 minute at 2025° C. The columns are then discarded, and the eluted RNA stored at −10° C. or lower.

Procedure for real-time RT-PCR reactions. The Master Mix for the reverse transcription was prepared (volume reagent per sample) (10×RT Buffer (2 µL), dNTPs (4 µL), Primer HRV-R1 (10 µM working conc.) (2 µL), RNAsin (0.4 µL), M-MuLV Reverse Transcriptase (0.4 µL), and RNAse-free dH$_2$O (1.2 µL)), and aliquots of 10 µL placed in each well of a 96-well Optical Reaction Plate. 10 µL of sample RNA, positive control RNA (HRV PC RNA) or negative control (dH$_2$O) were added to the appropriate wells. Reverse transcription was performed in a 9600 or 9700 thermocycler using the following cycling parameters: 42° C., 15 minutes; 99° C., 15 minutes; and 4° C., as needed. After reverse transcription was complete, the Reaction Plate was removed and centrifuged briefly to collect sample at the bottom of the well.

Real-Time PCR Master Mix (reagent volume per sample: 2× TaqMan Universal PCR Master Mix (25 mL), HRV-F1 Primer (10 µM working conc.) (2 mL), HRV-TM1 Probe (10 µM working conc.) (1 mL), and dH$_2$O (2 mL)) is prepared, and 30 µL aliquots added to each well containing reverse transcription reactions. After briefly centrifuging the plate to collect the reactions at the bottom of the wells and to eliminate any air bubbles, the samples are incubated using an ABI Prism Sequence Detection System using the following parameter: 50° C., 2 minutes; 95° C., 10 minutes; then 50 cycles of 95° C. for 15 sec and 60° C. for 1 minute. The results are then read and recorded.

Amplification of MS2 phage RNA spiked in patient specimens. In order to monitor sample preparation and to check whether inhibitory material is present in a given sample, 50 pg of MS2 RNA was spiked into each specimen prior to processing. The specimens are processed as described above and amplified separately using primers specific to MS2. MS2 reverse transcription used the same recipe for the master mix as that for HRV-RT with the exception that primer BS4 was used. MS2 PCR used the same master mix as HDV PCR except that primer BS3 was used.

The MS2 sequence to be amplified spans positions 160-325 of the MS2 genome such that amplification produces a 166 bp fragment, which can be visualized on a 2% agarose gel. The MS2 RNA must be amplified before the HRV RT-PCR result can be considered valid. Reagents used in the MS2 reverse transcription include: RNase free dH$_2$O (0.6 µL), dNTPs (4 µL), 10× reverse transcriptase buffer (1 µL), RNAsin (0.2 µL), Reverse transcriptase (0.2 µL), Downstream primer (BS4) (2 µL), and RNA sample (5 µL). Reverse transcription was carried out using the following parameters: 42° C., 15 minutes; 99° C., 15 minutes; and 4° C. as needed. Reagents for MS2 cDNA PCR included: Upstream primer (BS3) (2 µL), MgCl$_2$ (25 mM) 3 µL), Taq polymerase (5 U/µL) (0.25 µL), H$_2$O (30.75 µL), and 10×PCR buffer (4 µL). The parameters for PCR using a Perkin Elmer cycler 9600 or 9700 were as follows: 94° C., 1 minute; then 50 cycles of 94° C. (30 sec), 55° C. (30 sec), 72° C. (30 sec); 72° C. 10 minutes; and 4° C. as needed. MS2 RT-PCR product was detected on a 2% agarose gel containing ethidium bromide.

Reporting results. The HRV Positive Control, HRV PC, should report a $C_T$ value of less than 34 cycles. If the $C_T$ value of the positive control is higher than anticipated value, the assay run is considered Invalid. The Real-time RT-PCR process must be repeated on all samples beginning at the amplification step. The PCR Negative Control should always report a $C_T$ value equal to or greater than 40. If the $C_T$ value of the Negative Control is less than 40, the assay run is considered Invalid and no assay results will be reported. Real-time PCR process must be repeated on all samples beginning at the amplification step. Likewise, the Extraction Negative Control should always report a $C_T$ value equal to or greater than 40. If the $C_T$ value is less than 40, the assay is considered Invalid and no assay results will be reported. The entire extraction process and amplification needs to be repeated on all samples from the affected run. MS2 RNA should also be detected as an indicator of successful amplification. Unsuccessful amplification can result from, for example, mistake(s) been made during run, or the presence of inhibitory material in the sample (thus requiring re-extraction of the sample).

Once the criteria regarding the positive and negative controls are satisfied, the HRV RNA in patient samples can then be examined. If the $C_T$ value of a patient specimen is less than 36, the result is reported as "Detected". If the $C_T$ value of a patient specimen is equal to or greater than 38.01, the result is reported as "Not Detected". If the $C_T$ value of a patient specimen is between 36 and 38, the result is considered equivocal (neither positive nor negative). The HRV real-time RT-PCR amplification and detection for the extracted RNA of an equivocal specimen is repeated. If the $C_T$ value for the second amplification is less than 36, the result is reported as "Detected". If the $C_T$ value for the second amplification is 38.01 or greater, the result is reported as "Not Detected". If the $C_T$ value for the second amplification is again between 36 and 38.00, the result is reported as "Equivocal".

Example

This example describes the validation of the real-time RT-PCR assay for the detection of HRVs RNA from nasopharyngeal aspirates (NPA), bronchial washing/bronchoalveolar lavage (BAL) and swab specimens. The HRV virus Real-Time RT-PCR assay methodology used was as described above.

A target sequence was identified by aligning the 5' untranslated region (UTR) of 33 different HRV isolates, as well as from isolates of non-HRV picronaviruses including enterovirus, poliovirus, and coxsackie virus (see FIGS. 3A-3D). A conserved 5' UTR region of the HRV genome was identified, and a target sequence identified, as shown in FIG. 1. Primers and probes were designed so that the assay detected majority of the HRV serotypes, while at the same time avoiding detection of other picronaviruses, including the closely related EVs. Exemplary of such primers and probes are those described in the materials and methods section above, and which are used in the assays to provide the results below.

As illustrated in detail below, the primer/probe set exemplified below detected 17 out of the 18 HRV reference strains obtained from ATCC, which strains are representative of different HRV subgroups (see FIGS. 3A and 3B). The 17 HRV serotypes detected were: 1A, 2, 12, 13, 14, 16, 21, 39, 45, 52, 55, 66, 69, 84, 88, 91 and 100. HRV serotype 87, which was not detected in this assay, has been reported to be more closely related to EVs. The EVs tested, and proven not detectable by this assay, included echovirus 6, 7 and 11 enterovirus 71, coxsackievirus A7, A9, A16, B1 and B5, poliovirus 1 and 2.

Nasopharyngeal aspirates (NPA), bronchial washing, bronchoalveolar lavage (BAL) and swab specimens were obtained from Valuable Specimen Bank (VSB) of Focus Technologies, Inc. and RNA/DNA samples extracted from patient samples were obtained from the Molecular Diagnostics Laboratory of Focus Technologies. RNA was isolated from 140 μL of each patient specimen using the QIAGEN QIAamp Viral RNA Mini kit as described above.

Verification of Reference Range. In order to verify the Reference Range criteria of the assay, HRV-negative NPA and swab specimens were assayed as described above, and the $C_T$ value for each specimen documented. Results of these assays were used to determine the expected values that will be used to report a negative result.

Verification of Analytical Specificity. Analytical Specificity is defined as the ability of the assay to discriminate between the rhinovirus RNA target and the genomic DNA or RNA of related viruses or other pathogenic or commensal flora found in the specimen types being assayed. For verification of the Analytical Specificity criteria of the assay, genomic DNA or RNA of related viruses or pathogens possibly found in NPA, swab or BAL were amplified and detected as described above. Genomic DNA or RNA from Echovirus 6, 7 11 and 71, coxsackievirus A7, A9, A16, B1 and B5, poliovirus 1, poliovirus 2, influenza A and B, parainfluenza 3, adenovirus, SARS coronavirus, human coronaviruses 229E and OC43, West Nile virus, human metapneumovirus and rubella virus were obtained from the Molecular Diagnostics Laboratory of Focus Technologies. Verification of the specificity of rhinovirus was done using reference strains of several serotypes obtained from American Type Culture Collections. Ten μL of DNA or RNA of each sample was assayed as described above and the $C_T$ value for each sample was documented.

Verification of Analytical Sensitivity. RNA samples extracted from NPA, swab or BAL specimens spiked with known quantity of HRV target were assayed to determine the lower limit of detection of the assay.

Verification of Reportable Range. For verification of Reportable Range, HRV-positive NPA, BAL and swab specimens were obtained from the Molecular Diagnostics or Virology Laboratory of Focus Technologies and assayed as described above. The $C_T$ Values generated by the specimens should be indicative of positive specimens tested by this assay.

Verification of Precision. To verify the repeatability of the assay, independent RNA extractions were performed on each of a sample from NPA, swab and BAL spiked with HRV and from the respective non-spiked matrix. Five independent real-time RT-PCRs were performed on each of the extracted RNA as described above. The $C_T$ values from the 5 RT-PCR were averaged for each specimen. The experiment was then repeated 7 additional times for between-run precision.

Verification of Accuracy. To satisfy this criterion of the verification, blind panel containing HRV-positive or HRV-negative NPA, swab and BAL samples were assayed as described above and their results were compared to the unveiled HRV status of the samples.

Results

Reference Range. In order to determine the range of the threshold cycle ($C_T$) value of HRV-negative specimens, 10 μl of RNA/DNA extracted from NPA, BAL and swab specimens expected to be HRV-negative was subjected to 50 cycles of real-time RT-PCR as described above. These specimens were determined to be rhinovirus RNA-negative by the absence of the 93 b.p. PCR fragment using a separate set of primers in a conventional RT-PCR assay as described in the literature (Billaud G., et al, 2003). Table 1 lists the individual patient specimens and the results of $C_T$ values. The $C_T$ value (or "cycle threshold") is the number of the PCR cycle at which a statistically significant increase in reporter fluorescence can be detected above the baseline. Given that all suspected HRV-negative specimens evaluated here consistently have $C_T$ value of 50 after 50 cycles of PCR, it was determined that test specimens with $C_T$ values of 50 are HRV-negative and can be reported as such.

TABLE 1

| SPECIMEN TYPE | Specimen ID | $C_T$ Value |
|---|---|---|
| NPA | NPA-1 | 50 |
| NPA | NPA-2 | 50 |
| NPA | NPA-3 | 50 |
| NPA | NPA-4 | 50 |
| NPA | NPA-5 | 50 |
| NPA | NPA-6 | 50 |
| NPA | NPA-7 | 50 |
| NPA | NPA-8 | 50 |
| NPA | NPA-9 | 50 |
| Swab | Swab-1 | 50 |
| Swab | Swab-2 | 50 |
| Swab | Swab-3 | 50 |
| Swab | Swab-4 | 50 |
| Swab | Swab-5 | 50 |
| Swab | Swab-6 | 50 |
| Swab | Swab-7 | 50 |
| Swab | Swab-8 | 50 |
| Swab | Swab-9 | 50 |
| BAL | Bal-1 | 50 |
| BAL | Bal-2 | 50 |
| BAL | Bal-3 | 50 |
| BAL | Bal-4 | 50 |
| BAL | Bal-5 | 50 |
| BAL | Bal-6 | 50 |
| BAL | Bal-7 | 50 |
| BAL | Bal-8 | 50 |
| BAL | Bal-9 | 50 |
| BAL | Bal-10 | 50 |
| NPA | NPA-10 | 50 |
| NPA | NPA-11 | 50. |
| NPA | NPA-12 | 50 |
| NPA | NPA-13 | 50 |
| NPA | NPA-15 | 50 |
| NPA | NPA-17 | 50 |
| NPA | NPA-18 | 50 |
| NPA | NPA-19 | 50 |
| Swab | Swab-10 | 50 |
| Swab | Swab-11 | 50 |
| Swab | Swab-12 | 50 |
| Swab | Swab-13 | 50 |
| Swab | Swab-14 | 50 |
| Swab | Swab-15 | 50 |
| Swab | Swab-16 | 50 |
| Swab | Swab-17 | 50 |
| Swab | Swab-18 | 50 |
| Swab | Swab-19 | 50 |
| BAL | Bal-11 | 50 |
| BAL | Bal-12 | 50 |
| BAL | Bal-13 | 50 |
| BAL | Bal-14 | 50 |
| BAL | Bal-15 | 50 |
| BAL | Bal-16 | 50 |
| BAL | Bal-17 | 50 |
| BAL | Bal-18 | 50 |
| BAL | Bal-19 | 50 |
| BAL | Bal-20 | 50 |

Analytical Specificity. Aliquots of RNA or DNA of 18 serotypes of HRVs, Echovirus 6, 7, 11 and 71, coxsackievirus A7, A9, A16, B1 and B5, poliovirus 1, poliovirus 2, influenza A and B, parainfluenza 3, adenovirus, SARS coronavirus, human coronavirus 229E and OC43, West Nile virus, human metapneumovirus (hMPV) and rubella virus were amplified and detected as described above, and the results are shown in Table 2. While 17 of the 18 HRVs have $C_T$ values between 12 and 26, all other samples have $C_T$ values at or above 40. The serotype 87, not detectable by this assay, had been reported to be more closely related to EVs than to other HRVs (Savolainen C., et al., 2002). These results confirm that the developed primers and probe are specific for the rhinovirus target.

TABLE 2

| Pathogen | $C_T$ Value | Pathogen | $C_T$ Value |
|---|---|---|---|
| HRV-1A | 23.71 | HRV-52 | 17.60 |
| HRV-2 | 13.23 | HRV-55 | 19.56 |
| HRV-12 | 22.86 | HRV-66 | 16.90 |
| HRV-13 | 14.79 | HRV-69 | 15.13 |
| HRV-14 | 12.09 | HRV-84 | 21.14 |
| HRV-16 | 14.37 | HRV-87 | 50 |
| HRV-21 | 19.76 | HRV-88 | 16.49 |
| HRV-39 | 22.24 | HRV-91 | 17.53 |
| HRV-45 | 25.94 | HRV-100 | 15.89 |
| Echovirus 6 | 50 | Poliovirus 1 | 50 |
| Echovirus 7 | 50 | Poliovirus 2 | 40.54 |
| Echovirus 11 | 50 | Influenza A | 50 |
| Echovirus 71 | 44.45 | Influenza B | 43.41 |
| Coxsackievirus A7 | 50 | Parainfluenza 3 | 50 |
| Coxsackievirus A9 | 41.02 | Adenovirus | 50 |
| Coxsackievirus A16 | 50 | SARS | 40.48 |
| Coxsackievirus B1 | 50 | Coronavirus 229E | 50 |
| Coxsackievirus B5 | 50 | Coronavirus OC43 | 50 |
| West Nile Virus | 50 | hMPV | 50 |
| Rubella | 47.04 | | |

$C_T$ Value: PCR cycle at which a statistically significant increase in reporter fluorescence can be detected above the baseline.

Analytical Sensitivity. NPA, BAL and swab specimens spiked with known quantity of HRV targets were assayed to determine the lower limit of detection of the assay. Serial diluted rhinoviruses were spiked into pooled HRV-negative NPA, BAL or swab samples and RNA was extracted from 140 μL of each dilution series. The extracted RNAs (10 μL of the 60 μL extracted RNA) were assayed in four (4) separate assay runs to determine the lower limit of detection.

The results are shown in Table 3. Data from the 4 separate runs show that the $C_T$ values for each specimen are relatively reproducible. For all types of specimens, the real-time HRV RT-PCR shows positive results when there are 200 copies of HRV in the RT-PCR reaction. However the limit of linear range detection ends at $2 \times 10^4$ copies of RNA, which is equivalent to $9 \times 10^5$ copies of RNA per mL of specimen.

TABLE 3

| HRV-spiked Dilutions | Input HRV RNA copies* | Input HRV RNA copies/mL of specimen | Average $C_T$ NPA | Average $C_T$ SWAB | Average $C_T$ BAL |
|---|---|---|---|---|---|
| 1:10 | $2.1 \times 10^9$ | $9.0 \times 10^{10}$ | 18.19 | 18.93 | 18.77 |
| 1:10² | $2.1 \times 10^8$ | $9.0 \times 10^9$ | 21.90 | 21.96 | 22.36 |
| 10) | | | | | |
| 1:10³ | $2.1 \times 10^7$ | $9.0 \times 10^8$ | 24.73 | 25.58 | 25.37 |
| 1:10⁴ | $2.1 \times 10^6$ | $9.0 \times 10^7$ | 28.84 | 29.25 | 28.47 |
| 1:10⁵ | $2.1 \times 10^5$ | $9.0 \times 10^6$ | 32.12 | 34.19 | 32.97 |
| 1:10⁶ | $2.1 \times 10^4$ | $9.0 \times 10^5$ | 34.61 | 37.76 | 35.63 |
| 1:10⁷ | $2.1 \times 10^3$ | $9.0 \times 10^4$ | 36.62 | 38.93 | 36.57 |
| 1:10⁸ | $2.1 \times 10^2$ | $9.0 \times 10^3$ | 37.97 | 39.93 | 39.03 |

$C_T$ Values are the average from 4 independent RT-PCR performed on each extracted RNA.
*The original HRV RNA copy number was extrapolated from a standard curve generated from quantified in-vitro transcribed RNA run in parallel.

Reportable Range. The Reportable Range and Analytical Sensitivity parameters of an assay define the cut-off values for reporting positive and negative results for specimens tested by the assay. The Reportable Range of the HRV RNA real-time RT-PCR assay is determined by testing rhinovirus RNA-positive specimens using the procedure described above. These RNA samples extracted from HRV-positive NPA, BAL and swab specimens were obtained from Virology Laboratory of Focus Technologies. These specimens were determined to be rhinovirus RNA-positive by the presence of the 93 b.p. PCR fragment using conventional RT-PCR assay as described in the literature (Billaud G., et al, 2003). The results for the HRV RNA-positive specimens are shown in Table 4. For all HRV RNA-positive specimens tested, the $C_T$ value range was between 18 to 35.

TABLE 4

| Specimen Type | Accession Number | $C_T$ Value | Specimen Type | Accession Number | $C_T$ Value |
|---|---|---|---|---|---|
| NPA | NPA-20 | 32.27 | NPA | NPA-28 | 26.03 |
| BAL | BAL-21 | 30.36 | NPA | NPA-29 | 17.4 |
| NPA | NPA-21 | 25.17 | BAL | BAL-23 | 28.33 |
| NPA | NPA-22 | 28.48 | NPA | NPA-30 | 23.84 |
| NPA | NPA-23 | 32.19 | NPA | NPA-31 | 24.72 |
| BAL | BAL-22 | 29.26 | NPA | NPA-32 | 30.25 |
| NPA | NPA-24 | 26.71 | NPA | NPA-33 | 26.29 |
| NPA | NPA-25 | 23.69 | NPA | NPA-34 | 23.41 |
| NPA | NPA-26 | 25.45 | Swab | Swab-20 | 24.54 |
| NPA | NPA-27 | 35.17 | BAL | BAL-24 | 32.07 |
| NPA | NPA-14 | 33.65 | NPA | NPA-16 | 34.81 |

$C_T$ Value: PCR cycle at which a statistically significant increase in reporter fluorescence can be detected above the baseline.

Precision. In order to validate the Precision criteria of the HRV real-time RT-PCR assay, rhinovirus-positive and -negative specimens (NPA, BAL and swabs) were obtained and allocated into 8 separate 200 µL aliquots. RNA was extracted from each aliquot and assayed as described above in 8 separate assay runs. Five independent RT-PCRs were performed on each of the extracted RNA. The averaged $C_T$ values from the five RT-PCR of each sample are shown in Table 5. The results show excellent between-run reproducibility of the assay, with % CV values of less than 2% for each specimen type tested.

TABLE 5

| | HRV-Positive NPA | HRV-Negative NPA | HRV-Positive Swab | HRV-Negative Swab | HRV-Positive BAL | HRV-Negative BAL |
|---|---|---|---|---|---|---|
| Run 1 | 27.59 | 50 | 26.74 | 50 | 27.62 | 50 |
| Run 2 | 27.45 | 50 | 27.04 | 50 | 27.61 | 44.11 |
| Run 3 | 27.71 | 50 | 27.41 | 50 | 27.40 | 45.81 |
| Run 4 | 27.14 | 50 | 26.30 | 50 | 27.76 | 49.05 |
| Run 5 | 26.95 | 50 | 26.55 | 50 | 27.86 | 50 |
| Run 6 | 27.47 | 47.60 | 26.83 | 49.07 | 27.56 | 50 |
| Run 7 | 27.75 | 50 | 27.04 | 48.70 | 28.88 | 49.52 |
| Run 8 | 27.70 | 50 | 27.17 | 49.78 | 28.54 | 48.27 |
| Mean | 27.47 | 49.70 | 26.89 | 49.69 | 27.90 | 48.35 |
| % CV | 1.05% | 1.70% | 1.31% | 1.04% | 1.88% | 4.59% |

$C_T$ Values are the average from 5 independent RT-PCR performed on each extracted RNA.

Accuracy. In order to verify the accuracy of the HRV real-time RT-PCR assay, a blind panel consisting of HRV-spiked as well as non-spiked NPA, BAL and swab samples were evaluated. RNA was extracted from these samples and subjected to real-time RT-PCR as described above. The resulting HRV status, as determined from the $C_T$ value is compared to the unveiled results as shown in Table 6.

Using the results of the reference range, analytical sensitivity and reportable range studies, the following interpretative rules were established for Ct values determined by the HRV real-time RT-PCR:

| | |
|---|---|
| Ct value < than 36 | Result = Detected |
| Ct value 36.00-38.00 | Result = Equivocal |
| Ct value = or > than 38.1 | Result = Not Detected |

Using the above criteria, the HRV real-time RT-PCR assay produced a result that is in 100% agreement between the HRV status as determined using the method described above and the disclosed panel except Sample #118 which was spiked with virus at a concentration close to the detection limit of the assay.

TABLE 6

| Sample # | Matrix | RT-PCR ($C_T$) | HRV Status based on RT-PCR | HRV Status (Un-blinded Panel) |
|---|---|---|---|---|
| 102 | Swab | 30.97 | Detected | Spiked w/ 1.3 × $10^5$ copies HRV16 |
| 103 | Swab | 40.32 | Not Detected | Non-spiked |
| 104 | Swab | 44.23 | Not Detected | Non-spiked |
| 105 | Swab | 21.98 | Detected | Spiked w/ 1.3 × $10^6$ copies HRV16 |
| 106 | Swab | 32.26 | Detected | Spiked w/ 1.3 × $10^4$ copies HRV16 |
| 108 | Swab | 33.50 | Detected | Spiked w/ 1.3 × $10^3$ copies HRV16 |
| 109 | Swab | 42.32 | Not Detected | Non-spiked |
| 110 | Swab | 41.10 | Not Detected | Non-spiked |
| 112 | NPA | 27.68 | Detected | Spiked w/ 1.3 × $10^5$ copies HRV16 |
| 113 | NPA | 48.50 | Not Detected | Non-spiked |
| 114 | NPA | 49.15 | Not Detected | Non-spiked |
| 115 | NPA | 24.55 | Detected | Spiked w/ 1.3 × $10^6$ copies HRV16 |
| 116 | NPA | 31.92 | Detected | Spiked w/ 1.3 × $10^4$ copies HRV16 |
| 118 | NPA | 37.16 | Equivocal | Spiked w/ 1.3 × $10^3$ copies HRV16 |
| 119 | NPA | 50 | Not Detected | Non-spiked |
| 120 | NPA | 50 | Not Detected | Non-spiked |
| 122 | BAL | 27.53 | Detected | Spiked w/ 1.3 × $10^5$ copies HRV16 |
| 123 | BAL | 41.80 | Not Detected | Non-spiked |

TABLE 6-continued

| Sample # | Matrix | RT-PCR ($C_T$) | HRV Status based on RT-PCR | HRV Status (Un-blinded Panel) |
|---|---|---|---|---|
| 124 | BAL | 43.91 | Not Detected | Non-spiked |
| 125 | BAL | 22.85 | Detected | Spiked w/ 1.3 × 10$^6$ copies HRV16 |
| 126 | BAL | 31.59 | Detected | Spiked w/ 1.3 × 10$^4$ copies HRV16 |
| 128 | BAL | 34.45 | Detected | Spiked w/ 1.3 × 10$^3$ copies HRV16 |
| 129 | BAL | 39.4 | Not Detected | Non-spiked |
| 130 | BAL | 41.25 | Not Detected | Non-spiked |

$C_T$ Values are the average from 5 independent RT-PCR performed on each extracted RNA.

CONCLUSION

The results shown demonstrate that the invention provides an assay that is sensitive, specific, accurate and reproducible assay for the rapid detection of human rhinovirus RNA in NPA, BAL and swab specimens.

It is evident from the above results and discussion that the subject invention provides an important new means for the detection of HRV. As such, the subject methods and systems find use in a variety of different applications, including research, medical, therapeutic, and other applications.

Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for detecting human rhinovirus (HRV) nucleic acid in a sample, comprising amplifying an HRV nucleic acid from said sample and detecting the presence of the amplified nucleic acid wherein said amplifying and detecting is achieved using oligonucleotides designed to specifically hybridize to the target sequence of HRV shown as SEQ ID NO: 7 or a full complement thereof, wherein the at least one oligonucleotide selectively binds HRV nucleic acids but not enterovirus nucleic acids.

2. The method of claim 1, wherein at least one of said oligonucleotides is a degenerate oligonucleotide.

3. The method of claim 1, wherein said oligonucleotides comprise a first primer, a second primer, and a probe.

4. The method of claim 3, wherein each of said oligonucleotides is degenerate.

5. The method of claim 1, wherein said target nucleic acid comprises the sequence of SEQ ID NO: 12, or full complement thereof.

6. The method of claim 1, wherein said target nucleic acid comprises the sequence of SEQ ID NO: 6, or full complement thereof.

7. The method of claim 1, wherein said target nucleic acid comprises the sequence of SEQ ID NO: 11, or full complement thereof.

8. The method of claim 3, wherein said first primer comprising the sequence set forth in SEQ ID NO: 8, or the full complement thereof.

9. The method of claim 3, wherein said first primer comprises the sequence set forth in SEQ ID NO: 13, or full complement thereof.

10. The method of claim 3, wherein said second primer comprising the sequence set forth in SEQ ID NO.: 9, or full complement thereof.

11. The method of claim 3, wherein said second primer comprises the sequence set forth in SEQ ID NO: 14, or full complement thereof.

12. The method of claim 3, wherein said probe comprises the sequence set forth in SEQ ID NO.: 10, or the full complement thereof.

13. The method of claim 3, wherein said probe comprises a sequence set forth in SEQ ID NO: 18.

14. A method of claim 1, comprising:
   (a) contacting said sample with
      (i) a first oligonucleotide primer comprising the sequence set forth in SEQ ID NO: 8, or a full complement thereof, and
      (ii) a second oligonucleotide primer comprising the sequence set forth in SEQ ID NO: 9 or a full complement thereof,
   (b) conducting an amplification reaction using said first and second oligonucleotide primers to produce a target nucleic acid product;
   (c) hybridizing to said target nucleic acid an oligonucleotide probe comprising the sequence set forth in SEQ ID NO.: 10, wherein said probe further comprises a detectable label.
   (d) detecting the hybridization of said probe and said target nucleic acid, wherein hybridization is indicative of the presence of HRV nucleic acid.

15. The method of claim 14, wherein said first primer comprises the sequence set forth in SEQ ID NO: 13, or full complement thereof.

16. The method of claim 14, wherein said second primer comprises the sequence set forth in SEQ ID NO: 14, or full complement thereof.

17. The method of claim 14, wherein said probe comprises the sequence set forth in SEQ ID NO: 18, or full complement thereof.

18. The method of claim 14, wherein said detectable label comprises a fluorescent label.

19. The method of claim 18, wherein said amplifying step (b) and said hybridizing step (c), and wherein said detecting step (d) is performed in real-time.

20. The method of claim 19, wherein said hybridizing step (c) is performed in the presence of a 5'-exonuclease activity and wherein said probe further comprises a quenching moiety.

21. The method of claim 14, further comprising at least two of the following:
   said first primer comprising the sequence set forth in SEQ ID NO: 13, or full complement thereof,
   said second primer comprising the sequence set forth in SEQ ID NO: 14, or full complement thereof, and,
   said probe comprising the sequence set forth in SEQ ID NO: 18, or full complement thereof.

22. The method of claim 14, wherein said first primer comprises the sequence set forth in SEQ ID NO: 13, or full complement thereof; said second primer comprises the sequence set forth in SEQ ID NO: 14, or full complement thereof, and, said probe comprises the sequence set forth in SEQ ID NO: 18, or full complement thereof.

23. The method of claim 1, wherein the oligonucleotides are hybridized under stringent hybridization conditions.

* * * * *

SEQUENCE LISTING

```
<160> NUMBER OF SEQ ID NOS: 74

<210> SEQ ID NO 1
<211> LENGTH: 72
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: 28
<223> OTHER INFORMATION: n = A,T,C or G

<400> SEQUENCE: 1
ggtgtgaaga sycvcrtgtg ctcacttntg agtcctccgg cccctgaatg cggctaacct      60
waamccyrsa gc                                                          72

<210> SEQ ID NO 2
<211> LENGTH: 72
<212> TYPE: RNA
<213> ORGANISM: human rhinovirus
<220> FEATURE:
<221> NAME/KEY: misc_feature
<222> LOCATION: (28)...(28)
<223> OTHER INFORMATION: n = A,U,C or G

<400> SEQUENCE: 2
ggugugaaga sycvcrugug cucacuunug aguccuccgg ccccugaaug cggcuaaccu      60
waamccyrsa gc                                                          72

<210> SEQ ID NO 3
<211> LENGTH: 72
<212> TYPE: DNA
<213> ORGANISM: enterovirus
<220> FEATURE:
<221> NAME/KEY: misc_feature
```

<222> LOCATION: (28)...(28)
<223> OTHER INFORMATION: n = A, T, C or G

<400> SEQUENCE: 3
ggtgygaaga gcctattgag ctcacttnrk artcctccgg ccctgaatg cggctaatcc    60 taacyrcgga gc                                                      72

<210> SEQ ID NO 4
<211> LENGTH: 73
<212> TYPE: DNA
<213> ORGANISM: human rhinovirus
<220> FEATURE:
<221> NAME/KEY: misc_feature
<222> LOCATION: (5)...(5)
<223> OTHER INFORMATION: n = T
<220> FEATURE:
<221> NAME/KEY: misc_feature
<222> LOCATION: (11)...(11)
<223> OTHER INFORMATION: n = G or C
<220> FEATURE:
<221> NAME/KEY: misc_feature
<222> LOCATION: (12)...(12)
<223> OTHER INFORMATION: n = C or T
<220> FEATURE:
<221> NAME/KEY: misc_feature
<222> LOCATION: (14)...(14)
<223> OTHER INFORMATION: n = A, C, or G
<220> FEATURE:
<221> NAME/KEY: misc_feature
<222> LOCATION: (15)...(15)
<223> OTHER INFORMATION: n = C
<220> FEATURE:
<221> NAME/KEY: misc_feature
<222> LOCATION: (16)...(16)
<223> OTHER INFORMATION: n = G or A
<220> FEATURE:
<221> NAME/KEY: misc_feature
<222> LOCATION: (19)...(19)
<223> OTHER INFORMATION: n = T
<220> FEATURE:
<221> NAME/KEY: misc_feature
<222> LOCATION: (28)...(28)
<223> OTHER INFORMATION: n = A, T, C, or G
<220> FEATURE:
<221> NAME/KEY: misc_feature
<222> LOCATION: (30)...(30)
<223> OTHER INFORMATION: n = T
<220> FEATURE:
<221> NAME/KEY: misc_feature
<222> LOCATION: (31)...(31)
<223> OTHER INFORMATION: n = G
<220> FEATURE:
<221> NAME/KEY: misc_feature
<222> LOCATION: (33)...(33)
<223> OTHER INFORMATION: n = G
<220> FEATURE:
<221> NAME/KEY: misc_feature
<222> LOCATION: (59)...(59)
<223> OTHER INFORMATION: n = C
<220> FEATURE:
<221> NAME/KEY: misc_feature
<222> LOCATION: (61)...(61)
<223> OTHER INFORMATION: n = T
<220> FEATURE:
<221> NAME/KEY: misc_feature
<222> LOCATION: (62)...(62)
<223> OTHER INFORMATION: n = A or T
<220> FEATURE:
<221> NAME/KEY: misc_feature
<222> LOCATION: (65)...(65)
<223> OTHER INFORMATION: n = A or C
<220> FEATURE:
<221> NAME/KEY: misc_feature
<222> LOCATION: (66)...(66)
<223> OTHER INFORMATION: n = C
<220> FEATURE:
<221> NAME/KEY: misc_feature

```
<222> LOCATION: (67)...(67)
<223> OTHER INFORMATION: n = C
<220> FEATURE:
<221> NAME/KEY: misc_feature
<222> LOCATION: (68)...(68)
<223> OTHER INFORMATION: n = C or T
<220> FEATURE:
<221> NAME/KEY: misc_feature
<222> LOCATION: (69)...(69)
<223> OTHER INFORMATION: n = A or G
<220> FEATURE:
<221> NAME/KEY: misc_feature
<222> LOCATION: (70)...(70)
<223> OTHER INFORMATION: n = C or G

<400> SEQUENCE: 4
ggtgngaaga nncnnntgng ctcacttntn nantcctccg gccccTgaat gcggctaanc      60
nnaannnnnn agc                                                        73

<210> SEQ ID NO 5
<211> LENGTH: 73
<212> TYPE: DNA
<213> ORGANISM: enterovirus
<220> FEATURE:
<221> NAME/KEY: misc_feature
<222> LOCATION: (5)...(5)
<223> OTHER INFORMATION: n = C or T
<220> FEATURE:
<221> NAME/KEY: misc_feature
<222> LOCATION: (11)...(11)
<223> OTHER INFORMATION: n = G
<220> FEATURE:
<221> NAME/KEY: misc_feature
<222> LOCATION: (12)...(12)
<223> OTHER INFORMATION: n = C
<220> FEATURE:
<221> NAME/KEY: misc_feature
<222> LOCATION: (14)...(14)
<223> OTHER INFORMATION: n = T
<220> FEATURE:
<221> NAME/KEY: misc_feature
<222> LOCATION: (15)...(15)
<223> OTHER INFORMATION: n = A
<220> FEATURE:
<221> NAME/KEY: misc_feature
<222> LOCATION: (16)...(16)
<223> OTHER INFORMATION: n = T
<220> FEATURE:
<221> NAME/KEY: misc_feature
<222> LOCATION: (19)...(19)
<223> OTHER INFORMATION: n = A
<220> FEATURE:
<221> NAME/KEY: misc_feature
<222> LOCATION: (28)...(28)
<223> OTHER INFORMATION: n = A, T, C or G
<220> FEATURE:
<221> NAME/KEY: misc_feature
<222> LOCATION: (30)...(30)
<223> OTHER INFORMATION: n = A or G
<220> FEATURE:
<221> NAME/KEY: misc_feature
<222> LOCATION: (31)...(31)
<223> OTHER INFORMATION: n = G or T
<220> FEATURE:
<221> NAME/KEY: misc_feature
<222> LOCATION: (33)...(33)
<223> OTHER INFORMATION: n = A or G
<220> FEATURE:
<221> NAME/KEY: misc_feature
<222> LOCATION: (59)...(59)
<223> OTHER INFORMATION: n = T
<220> FEATURE:
<221> NAME/KEY: misc_feature
<222> LOCATION: (61)...(61)
<223> OTHER INFORMATION: n = C
<220> FEATURE:
<221> NAME/KEY: misc_feature
```

```
<222> LOCATION: (62)...(62)
<223> OTHER INFORMATION: n = T
<220> FEATURE:
<221> NAME/KEY: misc_feature
<222> LOCATION: (65)...(65)
<223> OTHER INFORMATION: n = C
<220> FEATURE:
<221> NAME/KEY: misc_feature
<222> LOCATION: (66)...(66)
<223> OTHER INFORMATION: n = C or T
<220> FEATURE:
<221> NAME/KEY: misc_feature
<222> LOCATION: (67)...(67)
<223> OTHER INFORMATION: n = A or G
<220> FEATURE:
<221> NAME/KEY: misc_feature
<222> LOCATION: (68)...(68)
<223> OTHER INFORMATION: n = C
<220> FEATURE:
<221> NAME/KEY: misc_feature
<222> LOCATION: (69)...(69)
<223> OTHER INFORMATION: n = G
<220> FEATURE:
<221> NAME/KEY: misc_feature
<222> LOCATION: (70)...(70)
<223> OTHER INFORMATION: n = G

<400> SEQUENCE: 5
ggtgngaaga nncnnntgng ctcacttntn nantcctccg gccoctgaat gcggctaanc    60 nnaannnnnn agc                                                      73

<210> SEQ ID NO 6
<211> LENGTH: 73
<212> TYPE: DNA
<213> ORGANISM: human rhinovirus
<220> FEATURE:
<221> NAME/KEY: misc_feature
<222> LOCATION: (5)...(5)
<223> OTHER INFORMATION: n = A, T, or G
<220> FEATURE:
<221> NAME/KEY: misc_feature
<222> LOCATION: (11)...(11)
<223> OTHER INFORMATION: n = G or C
<220> FEATURE:
<221> NAME/KEY: misc_feature
<222> LOCATION: (12)...(12)
<223> OTHER INFORMATION: n = C or T
<220> FEATURE:
<221> NAME/KEY: misc_feature
<222> LOCATION: (14)...(14)
<223> OTHER INFORMATION: n = A, C or G
<220> FEATURE:
<221> NAME/KEY: misc_feature
<222> LOCATION: (15)...(15)
<223> OTHER INFORMATION: n = T, C or G
<220> FEATURE:
<221> NAME/KEY: misc_feature
<222> LOCATION: (16)...(16)
<223> OTHER INFORMATION: n = A, G or C
<220> FEATURE:
<221> NAME/KEY: misc_feature
<222> LOCATION: (19)...(19)
<223> OTHER INFORMATION: n = T
<220> FEATURE:
<221> NAME/KEY: misc_feature
<222> LOCATION: (28)...(28)
<223> OTHER INFORMATION: n = A, T, C or G
<220> FEATURE:
<221> NAME/KEY: misc_feature
<222> LOCATION: (30)...(30)
<223> OTHER INFORMATION: n = A, C or T
<220> FEATURE:
<221> NAME/KEY: misc_feature
<222> LOCATION: (31)...(31)
<223> OTHER INFORMATION: n = A, C or G
<220> FEATURE:
<221> NAME/KEY: misc_feature
```

<222> LOCATION: (33)...(33)
<223> OTHER INFORMATION: n = T, G or C
<220> FEATURE:
<221> NAME/KEY: misc_feature
<222> LOCATION: (59)...(59)
<223> OTHER INFORMATION: n = A, C or G
<220> FEATURE:
<221> NAME/KEY: misc_feature
<222> LOCATION: (61)...(61)
<223> OTHER INFORMATION: n = A, T or G
<220> FEATURE:
<221> NAME/KEY: misc_feature
<222> LOCATION: (62)...(62)
<223> OTHER INFORMATION: n = A or T
<220> FEATURE:
<221> NAME/KEY: misc_feature
<222> LOCATION: (65)...(65)
<223> OTHER INFORMATION: n = A or C
<220> FEATURE:
<221> NAME/KEY: misc_feature
<222> LOCATION: (66)...(66)
<223> OTHER INFORMATION: n = A, G, or C
<220> FEATURE:
<221> NAME/KEY: misc_feature
<222> LOCATION: (67)...(67)
<223> OTHER INFORMATION: n = T, G or C
<220> FEATURE:
<221> NAME/KEY: misc_feature
<222> LOCATION: (68)...(68)
<223> OTHER INFORMATION: n = C or T
<220> FEATURE:
<221> NAME/KEY: misc_feature
<222> LOCATION: (69)...(69)
<223> OTHER INFORMATION: n = A or G
<220> FEATURE:
<221> NAME/KEY: misc_feature
<222> LOCATION: (70)...(70)
<223> OTHER INFORMATION: n = C or G

<400> SEQUENCE: 6
ggtgngaaga nncnnntgng ctcacttntn nantcctccg gcccctgaat gcggctaanc      60
nnaannnnnn agc                                                        73

<210> SEQ ID NO 7
<211> LENGTH: 73
<212> TYPE: DNA
<213> ORGANISM: human rhinovirus
<220> FEATURE:
<221> NAME/KEY: misc_feature
<222> LOCATION: (5)...(5)
<223> OTHER INFORMATION: n = A, T or G
<220> FEATURE:
<221> NAME/KEY: misc_feature
<222> LOCATION: (11)...(11)
<223> OTHER INFORMATION: n = G or C
<220> FEATURE:
<221> NAME/KEY: misc_feature
<222> LOCATION: (12)...(12)
<223> OTHER INFORMATION: n = C or T
<220> FEATURE:
<221> NAME/KEY: misc_feature
<222> LOCATION: (14)...(14)
<223> OTHER INFORMATION: n = A, C or G
<220> FEATURE:
<221> NAME/KEY: misc_feature
<222> LOCATION: (15)...(15)
<223> OTHER INFORMATION: n = T, C or G
<220> FEATURE:
<221> NAME/KEY: misc_feature
<222> LOCATION: (16)...(16)
<223> OTHER INFORMATION: n = A, C or G
<220> FEATURE:
<221> NAME/KEY: misc_feature
<222> LOCATION: (19)...(19)
<223> OTHER INFORMATION: n = T
<220> FEATURE:
<221> NAME/KEY: misc_feature

```
<222> LOCATION: (23)...(29)
<223> OTHER INFORMATION: n = A,C,T or G
<220> FEATURE:
<221> NAME/KEY: misc_feature
<222> LOCATION: (30)...(30)
<223> OTHER INFORMATION: n = A, C or T
<220> FEATURE:
<221> NAME/KEY: misc_feature
<222> LOCATION: (31)...(31)
<223> OTHER INFORMATION: n = A, C or G
<220> FEATURE:
<221> NAME/KEY: misc_feature
<222> LOCATION: (33)...(33)
<223> OTHER INFORMATION: n = T, C or G
<220> FEATURE:
<221> NAME/KEY: misc_feature
<222> LOCATION: (52)...(52)
<223> OTHER INFORMATION: n = A,C,T or G
<220> FEATURE:
<221> NAME/KEY: misc_feature
<222> LOCATION: (59)...(59)
<223> OTHER INFORMATION: n = A, G or C
<220> FEATURE:
<221> NAME/KEY: misc_feature
<222> LOCATION: (61)...(61)
<223> OTHER INFORMATION: n = A, T or G
<220> FEATURE:
<221> NAME/KEY: misc_feature
<222> LOCATION: (62)...(62)
<223> OTHER INFORMATION: n = A or T
<220> FEATURE:
<221> NAME/KEY: misc_feature
<222> LOCATION: (65)...(65)
<223> OTHER INFORMATION: n = A or C
<220> FEATURE:
<221> NAME/KEY: misc_feature
<222> LOCATION: (66)...(66)
<223> OTHER INFORMATION: n = A, C or G
<220> FEATURE:
<221> NAME/KEY: misc_feature
<222> LOCATION: (67)...(67)
<223> OTHER INFORMATION: n = T, G or C
<220> FEATURE:
<221> NAME/KEY: misc_feature
<222> LOCATION: (68)...(68)
<223> OTHER INFORMATION: n = C or T
<220> FEATURE:
<221> NAME/KEY: misc_feature
<222> LOCATION: (69)...(69)
<223> OTHER INFORMATION: n = A or G
<220> FEATURE:
<221> NAME/KEY: misc_feature
<222> LOCATION: (70)...(70)
<223> OTHER INFORMATION: n = C or G

<400> SEQUENCE: 7
ggtgngaaga nncnnntgng ctnnnnnnnn nantcctccg gcccctgaat gnggctaanc      60
nnaannnnnn agc                                                        73

<210> SEQ ID NO 8
<211> LENGTH: 22
<212> TYPE: DNA
<213> ORGANISM: human rhinovirus
<220> FEATURE:
<221> NAME/KEY: misc_feature
<222> LOCATION: (5)...(5)
<223> OTHER INFORMATION: n = A, T or G
<220> FEATURE:
<221> NAME/KEY: misc_feature
<222> LOCATION: (11)...(11)
<223> OTHER INFORMATION: n = G or C
<220> FEATURE:
<221> NAME/KEY: misc_feature
<222> LOCATION: (12)...(12)
<223> OTHER INFORMATION: n = C or T
<220> FEATURE:
<221> NAME/KEY: misc_feature
```

<222> LOCATION: (14)...(14)
<223> OTHER INFORMATION: n = A, C or G
<220> FEATURE:
<221> NAME/KEY: misc_feature
<222> LOCATION: (15)...(15)
<223> OTHER INFORMATION: n = T, C or G
<220> FEATURE:
<221> NAME/KEY: misc_feature
<222> LOCATION: (16)...(16)
<223> OTHER INFORMATION: n = A, G, or C
<220> FEATURE:
<221> NAME/KEY: misc_feature
<222> LOCATION: (19)...(19)
<223> OTHER INFORMATION: n = T

<400> SEQUENCE: 8
ggtgngaaga nncnnntgng ct                                              22

<210> SEQ ID NO 9
<211> LENGTH: 21
<212> TYPE: DNA
<213> ORGANISM: human rhinovirus
<220> FEATURE:
<221> NAME/KEY: misc_feature
<222> LOCATION: (7)...(7)
<223> OTHER INFORMATION: n = A, C or G
<220> FEATURE:
<221> NAME/KEY: misc_feature
<222> LOCATION: (9)...(9)
<223> OTHER INFORMATION: n = A, G or T
<220> FEATURE:
<221> NAME/KEY: misc_feature
<222> LOCATION: (10)...(10)
<223> OTHER INFORMATION: n = A or T
<220> FEATURE:
<221> NAME/KEY: misc_feature
<222> LOCATION: (13)...(13)
<223> OTHER INFORMATION: n = A or C
<220> FEATURE:
<221> NAME/KEY: misc_feature
<222> LOCATION: (14)...(14)
<223> OTHER INFORMATION: n = A, C or G
<220> FEATURE:
<221> NAME/KEY: misc_feature
<222> LOCATION: (15)...(15)
<223> OTHER INFORMATION: n = C, T or G
<220> FEATURE:
<221> NAME/KEY: misc_feature
<222> LOCATION: (16)...(16)
<223> OTHER INFORMATION: n = C or T
<220> FEATURE:
<221> NAME/KEY: misc_feature
<222> LOCATION: (17)...(17)
<223> OTHER INFORMATION: n = A or G
<220> FEATURE:
<221> NAME/KEY: misc_feature
<222> LOCATION: (18)...(18)
<223> OTHER INFORMATION: n = C or G

<400> SEQUENCE: 9
ggctaancnn aannnnnnag c                                               21

<210> SEQ ID NO 10
<211> LENGTH: 22
<212> TYPE: DNA
<213> ORGANISM: human rhinovirus
<220> FEATURE:
<221> NAME/KEY: misc_feature
<222> LOCATION: (1)...(1)
<223> OTHER INFORMATION: n = A, T or C
<220> FEATURE:
<221> NAME/KEY: misc_feature
<222> LOCATION: (2)...(2)
<223> OTHER INFORMATION: n = A, C or G
<220> FEATURE:
<221> NAME/KEY: misc_feature

```
<222> LOCATION: (4)...(4)
<223> OTHER INFORMATION: n = T, C or G

<400> SEQUENCE: 10
nnantcctcc ggcccctgaa tg                                           22

<210> SEQ ID NO 11
<211> LENGTH: 73
<212> TYPE: DNA
<213> ORGANISM: human rhinovirus
<220> FEATURE:
<221> NAME/KEY: misc_feature
<222> LOCATION: (5)...(5)
<223> OTHER INFORMATION: n = T
<220> FEATURE:
<221> NAME/KEY: misc_feature
<222> LOCATION: (11)...(11)
<223> OTHER INFORMATION: n = G or C
<220> FEATURE:
<221> NAME/KEY: misc_feature
<222> LOCATION: (12)...(12)
<223> OTHER INFORMATION: n = C or T
<220> FEATURE:
<221> NAME/KEY: misc_feature
<222> LOCATION: (14)...(14)
<223> OTHER INFORMATION: n = A, C or G
<220> FEATURE:
<221> NAME/KEY: misc_feature
<222> LOCATION: (15)...(15)
<223> OTHER INFORMATION: n = C
<220> FEATURE:
<221> NAME/KEY: misc_feature
<222> LOCATION: (16)...(16)
<223> OTHER INFORMATION: n = G or A
<220> FEATURE:
<221> NAME/KEY: misc_feature
<222> LOCATION: (19)...(19)
<223> OTHER INFORMATION: n = T
<220> FEATURE:
<221> NAME/KEY: misc_feature
<222> LOCATION: (28)...(28)
<223> OTHER INFORMATION: n = A, T, C or G
<220> FEATURE:
<221> NAME/KEY: misc_feature
<222> LOCATION: (30)...(30)
<223> OTHER INFORMATION: n = T
<220> FEATURE:
<221> NAME/KEY: misc_feature
<222> LOCATION: (31)...(31)
<223> OTHER INFORMATION: n = G
<220> FEATURE:
<221> NAME/KEY: misc_feature
<222> LOCATION: (33)...(33)
<223> OTHER INFORMATION: n = G
<220> FEATURE:
<221> NAME/KEY: misc_feature
<222> LOCATION: (59)...(59)
<223> OTHER INFORMATION: n = C
<220> FEATURE:
<221> NAME/KEY: misc_feature
<222> LOCATION: (61)...(61)
<223> OTHER INFORMATION: n = T
<220> FEATURE:
<221> NAME/KEY: misc_feature
<222> LOCATION: (62)...(62)
<223> OTHER INFORMATION: n = A or T
<220> FEATURE:
<221> NAME/KEY: misc_feature
<222> LOCATION: (65)...(65)
<223> OTHER INFORMATION: n = A or C
<220> FEATURE:
<221> NAME/KEY: misc_feature
<222> LOCATION: (66)...(66)
<223> OTHER INFORMATION: n = C
<220> FEATURE:
<221> NAME/KEY: misc_feature
<222> LOCATION: (67)...(67)
<223> OTHER INFORMATION: n = C
```

```
<220> FEATURE:
<221> NAME/KEY: misc_feature
<222> LOCATION: (68)...(68)
<223> OTHER INFORMATION: n = C or T
<220> FEATURE:
<221> NAME/KEY: misc_feature
<222> LOCATION: (69)...(69)
<223> OTHER INFORMATION: n = A or G
<220> FEATURE:
<221> NAME/KEY: misc_feature
<222> LOCATION: (70)...(70)
<223> OTHER INFORMATION: n = C or G

<400> SEQUENCE: 11
ggtgngaaga nncnnntgng ctcacttntn nantcctccg gccccctgaat gcggctaanc    60 nnaannnnnn agc                                                       73

<210> SEQ ID NO 12
<211> LENGTH: 73
<212> TYPE: DNA
<213> ORGANISM: human rhinovirus
<220> FEATURE:
<221> NAME/KEY: misc_feature
<222> LOCATION: (5)...(5)
<223> OTHER INFORMATION: n = T
<220> FEATURE:
<221> NAME/KEY: misc_feature
<222> LOCATION: (11)...(11)
<223> OTHER INFORMATION: n = G or C
<220> FEATURE:
<221> NAME/KEY: misc_feature
<222> LOCATION: (12)...(12)
<223> OTHER INFORMATION: n = C or T
<220> FEATURE:
<221> NAME/KEY: misc_feature
<222> LOCATION: (14)...(14)
<223> OTHER INFORMATION: n = A, C or G
<220> FEATURE:
<221> NAME/KEY: misc_feature
<222> LOCATION: (15)...(15)
<223> OTHER INFORMATION: n = C
<220> FEATURE:
<221> NAME/KEY: misc_feature
<222> LOCATION: (16)...(16)
<223> OTHER INFORMATION: n = G or A
<220> FEATURE:
<221> NAME/KEY: misc_feature
<222> LOCATION: (19)...(19)
<223> OTHER INFORMATION: n = T
<220> FEATURE:
<221> NAME/KEY: misc_feature
<222> LOCATION: (23)...(29)
<223> OTHER INFORMATION: n = A,T,C or G
<220> FEATURE:
<221> NAME/KEY: misc_feature
<222> LOCATION: (30)...(30)
<223> OTHER INFORMATION: n = T
<220> FEATURE:
<221> NAME/KEY: misc_feature
<222> LOCATION: (31)...(31)
<223> OTHER INFORMATION: n = G
<220> FEATURE:
<221> NAME/KEY: misc_feature
<222> LOCATION: (33)...(33)
<223> OTHER INFORMATION: n = G
<220> FEATURE:
<221> NAME/KEY: misc_feature
<222> LOCATION: (52)...(52)
<223> OTHER INFORMATION: n = A,T,C or G
<220> FEATURE:
<221> NAME/KEY: misc_feature
<222> LOCATION: (59)...(59)
<223> OTHER INFORMATION: n = C
<220> FEATURE:
<221> NAME/KEY: misc_feature
<222> LOCATION: (61)...(61)
<223> OTHER INFORMATION: n = T
```

```
<220> FEATURE:
<221> NAME/KEY: misc_feature
<222> LOCATION: (62)...(62)
<223> OTHER INFORMATION: n = A or T
<220> FEATURE:
<221> NAME/KEY: misc_feature
<222> LOCATION: (65)...(65)
<223> OTHER INFORMATION: n = A or C
<220> FEATURE:
<221> NAME/KEY: misc_feature
<222> LOCATION: (66)...(66)
<223> OTHER INFORMATION: n = C
<220> FEATURE:
<221> NAME/KEY: misc_feature
<222> LOCATION: (67)...(67)
<223> OTHER INFORMATION: n = C
<220> FEATURE:
<221> NAME/KEY: misc_feature
<222> LOCATION: (68)...(68)
<223> OTHER INFORMATION: n = C or T
<220> FEATURE:
<221> NAME/KEY: misc_feature
<222> LOCATION: (69)...(69)
<223> OTHER INFORMATION: n = A or G
<220> FEATURE:
<221> NAME/KEY: misc_feature
<222> LOCATION: (70)...(70)
<223> OTHER INFORMATION: n = C or G

<400> SEQUENCE: 12
ggtgngaaga nncnnntgng ctnnnnnnnn nantcctccg gcccctgaat gnggctaanc      60
nnaannnnnn agc                                                         73

<210> SEQ ID NO 13
<211> LENGTH: 22
<212> TYPE: DNA
<213> ORGANISM: human rhinovirus
<220> FEATURE:
<221> NAME/KEY: misc_feature
<222> LOCATION: (5)...(5)
<223> OTHER INFORMATION: n = T
<220> FEATURE:
<221> NAME/KEY: misc_feature
<222> LOCATION: (11)...(11)
<223> OTHER INFORMATION: n = G or C
<220> FEATURE:
<221> NAME/KEY: misc_feature
<222> LOCATION: (12)...(12)
<223> OTHER INFORMATION: n = C or T
<220> FEATURE:
<221> NAME/KEY: misc_feature
<222> LOCATION: (14)...(14)
<223> OTHER INFORMATION: n = A, C or G
<220> FEATURE:
<221> NAME/KEY: misc_feature
<222> LOCATION: (15)...(15)
<223> OTHER INFORMATION: n = C
<220> FEATURE:
<221> NAME/KEY: misc_feature
<222> LOCATION: (16)...(16)
<223> OTHER INFORMATION: n = G or A
<220> FEATURE:
<221> NAME/KEY: misc_feature
<222> LOCATION: (19)...(19)
<223> OTHER INFORMATION: n = T

<400> SEQUENCE: 13
ggtgngaaga nncnnntgng ct                                               22

<210> SEQ ID NO 14
<211> LENGTH: 21
<212> TYPE: DNA
<213> ORGANISM: human rhinovirus
<220> FEATURE:
<221> NAME/KEY: misc_feature
```

```
<222> LOCATION: (7)...(7)
<223> OTHER INFORMATION: n = C
<220> FEATURE:
<221> NAME/KEY: misc_feature
<222> LOCATION: (9)...(9)
<223> OTHER INFORMATION: n = T
<220> FEATURE:
<221> NAME/KEY: misc_feature
<222> LOCATION: (10)...(10)
<223> OTHER INFORMATION: n = A or T
<220> FEATURE:
<221> NAME/KEY: misc_feature
<222> LOCATION: (13)...(13)
<223> OTHER INFORMATION: n = A or C
<220> FEATURE:
<221> NAME/KEY: misc_feature
<222> LOCATION: (14)...(14)
<223> OTHER INFORMATION: n = C
<220> FEATURE:
<221> NAME/KEY: misc_feature
<222> LOCATION: (15)...(15)
<223> OTHER INFORMATION: n = C
<220> FEATURE:
<221> NAME/KEY: misc_feature
<222> LOCATION: (16)...(16)
<223> OTHER INFORMATION: n = C or T
<220> FEATURE:
<221> NAME/KEY: misc_feature
<222> LOCATION: (17)...(17)
<223> OTHER INFORMATION: n = A or G
<220> FEATURE:
<221> NAME/KEY: misc_feature
<222> LOCATION: (18)...(18)
<223> OTHER INFORMATION: n = C or G

<400> SEQUENCE: 14
ggctaancnn aannnnnnag c                                              21

<210> SEQ ID NO 15
<211> LENGTH: 22
<212> TYPE: DNA
<213> ORGANISM: human rhinovirus
<220> FEATURE:
<221> NAME/KEY: misc_feature
<222> LOCATION: (1)...(1)
<223> OTHER INFORMATION: n = T
<220> FEATURE:
<221> NAME/KEY: misc_feature
<222> LOCATION: (2)...(2)
<223> OTHER INFORMATION: n = G
<220> FEATURE:
<221> NAME/KEY: misc_feature
<222> LOCATION: (4)...(4)
<223> OTHER INFORMATION: n = G

<400> SEQUENCE: 15
nnantcctcc ggcccctgaa tg                                             22

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
ggtgtgaaga sycvcrtgtg ct                                             22

<210> SEQ ID NO 17
<211> LENGTH: 21
<212> TYPE: DNA
<213> ORGANISM: Artificial Sequence
<220> FEATURE:
<223> OTHER INFORMATION: primer
```

-continued

<400> SEQUENCE: 17
gctsyrggkt twaggttagc c                                              21

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
tgagtcctcc ggcccctgaa tg                                             22

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
aacgagacct tcgtcccctc                                                20

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
ttaacgcccc ccgtgaatac g                                              21

<210> SEQ ID NO 21
<211> LENGTH: 415
<212> TYPE: DNA
<213> ORGANISM: human rhinovirus
<220> FEATURE:
<221> NAME/KEY: misc_feature
<222> LOCATION: 1, 23, 24, 25, 26, 27, 28, 29, 31, 32, 33, 34, 35, 44,
      60, 61, 135, 136, 137, 138, 139, 167, 203, 224, 225, 231, 232,
      284, 346, 390
<223> OTHER INFORMATION: n = A,T,C or G

<400> SEQUENCE: 21
ncaagcactt ctgtttcccc ggnnnnnnnt nnnnngctcc accnatgcca aaaacaattn     60
naatcgttat ccgcaaagtg actacgcaaa gcctagtaac atcttgtaag atttttggtt    120
ggtcgatcag gtgcnnnnna taccccccag tagacctggc agatganggc tggaaattcc    180
ccactggcga cagtgttcca gcnctgcgtg gctgcctgcc cacnncttat nnggtgtgaa    240
gccatatttt ggacatggtg tgaagagccg cgtgtgctca cttntgagtc ctccggcccc    300
tgaatgcggc taaccttaac cctgcagcca tggcacacaa tccagntgtg tttatggtcg    360
gaatgtaatg agcaattgcg ggatgggacn cgactacttt gggtgtccgt gtttc         415

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
ggtgtgaaga sycvcrtgtg ct                                             22

```
<210> SEQ ID NO 23
<211> LENGTH: 22
<212> TYPE: DNA
<213> ORGANISM: Artificial Sequence
<220> FEATURE:
<223> OTHER INFORMATION: probe

<400> SEQUENCE: 23
tgagtcctcc ggcccctgaa tg                                              22

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
ccgattggaw ttkggrystc g                                               21

<210> SEQ ID NO 25
<211> LENGTH: 22
<212> TYPE: DNA
<213> ORGANISM: enterovirus

<400> SEQUENCE: 25
ggtgygaaga gcctattgag ct                                              22

<210> SEQ ID NO 26
<211> LENGTH: 22
<212> TYPE: DNA
<213> ORGANISM: enterovirus

<400> SEQUENCE: 26
rkartcctcc ggcccctgaa tg                                              22

<210> SEQ ID NO 27
<211> LENGTH: 21
<212> TYPE: DNA
<213> ORGANISM: enterovirus

<400> SEQUENCE: 27
ggctaatcct aacyrcggag c                                               21

<210> SEQ ID NO 28
<211> LENGTH: 119
<212> TYPE: DNA
<213> ORGANISM: human rhinovirus

<400> SEQUENCE: 28
gggacgcctt aagtatgaca tggtgtgaag acccgcatgt gcttagctgt gagtcctccg     60
gcccctgaat gcggctaacc taaaccctgg agccttggag cacaagccag tgcttgcaa    119

<210> SEQ ID NO 29
<211> LENGTH: 118
<212> TYPE: DNA
<213> ORGANISM: human rhinovirus

<400> SEQUENCE: 29
gtgaagccaa ggattggaca gggtgtgaag agccgcgtgt gctcgctttg agtcctccgg    60
cccctgaatg cggctaacct taaacctgca gccatggctc ataagccaat gagtttat     118
```

```
<210> SEQ ID NO 30
<211> LENGTH: 118
<212> TYPE: DNA
<213> ORGANISM: human rhinovirus

<400> SEQUENCE: 30
gtgaagccaa acaatggaca gggtgtgaag agccgcgtgt gctcgctttg agtcctccgg      60
cccctgaatg cggctaacct taaacctgca gccattgctc acaatccagt gagttagt       118

<210> SEQ ID NO 31
<211> LENGTH: 118
<212> TYPE: DNA
<213> ORGANISM: human rhinovirus

<400> SEQUENCE: 31
gtgaagccag aatttcgaca aggtgtgaag agccgcgtgt gctcaccttg agtcctccgg      60
cccctgaatg cggctaacct taaacccgca gccatggtcc acaaaccagt ggatgtat       118

<210> SEQ ID NO 32
<211> LENGTH: 118
<212> TYPE: DNA
<213> ORGANISM: human rhinovirus

<400> SEQUENCE: 32
gtgaagccaa atattggaca aggtgtgaag agccgcgtgt gctcatcttg agtcctccgg      60
cccctgaatg tggctaacct taaacctgca gccagtgcgc acaatccagt gtgtagct       118

<210> SEQ ID NO 33
<211> LENGTH: 118
<212> TYPE: DNA
<213> ORGANISM: human rhinovirus

<400> SEQUENCE: 33
gtgaagcctt aatttggaca gggtgcgaag agccgcgtgt gctcatcttg agtcctccgg      60
cccctgaatg cggctaacct taaacctgca gccattgttt gcaatccagc aaatatgt       118

<210> SEQ ID NO 34
<211> LENGTH: 118
<212> TYPE: DNA
<213> ORGANISM: human rhinovirus

<400> SEQUENCE: 34
gtgaagccag aatttcgaca aggtgtgaag agccgcgtgt gctcaccttg agtcctccgg      60
cccctgaatg cggctaacct taaacccgca gccatggtcc acaaaccagt ggatgtat       118

<210> SEQ ID NO 35
<211> LENGTH: 119
<212> TYPE: DNA
<213> ORGANISM: human rhinovirus

<400> SEQUENCE: 35
gggacgccct tttaaggaca tggtgtgaag actcgcatgt gcttggttgt gagtcctccg      60 gccccctgaat gcggctaacc ttaaccctag agccttatgc cacgatccag tggttgtaa    119

<210> SEQ ID NO 36
<211> LENGTH: 118
<212> TYPE: DNA
<213> ORGANISM: human rhinovirus

<400> SEQUENCE: 36
gtgaagccaa agatcggaca gggtgtgaag agccgcgtgt gctcactttg agtcctccgg      60
```
cccctgaatg cggctaacct taaacctgca gccatggctc ataagccaat gagtttat        118

<210> SEQ ID NO 37
<211> LENGTH: 118
<212> TYPE: DNA
<213> ORGANISM: human rhinovirus

<400> SEQUENCE: 37
gtgaagccaa agattggaca gggtgtgaag agccgcgtgt gctcactttg agtcctccgg      60
cccctgaatg cggctaacct taaacctgca gccatggctc ataaaccaat gagcttat       118

<210> SEQ ID NO 38
<211> LENGTH: 118
<212> TYPE: DNA
<213> ORGANISM: human rhinovirus

<400> SEQUENCE: 38
gtgaagccaa acaatggaca aggtgtgaag agcccgtgt gctcgctttg agtcctccgg       60
cccctgaatg tggctaacct taaccctgca gctagagcac gtaacccaat gtgtatct      118

<210> SEQ ID NO 39
<211> LENGTH: 119
<212> TYPE: DNA
<213> ORGANISM: human rhinovirus

<400> SEQUENCE: 39
gggacgccct tttatagaca tggtgtgaag actcgcatgt gcttggttgt gattcctccg      60 gccccctgaat gcggctaacc ctaaccctgg agccttgtgt tacaaaccag taatattaa    119

<210> SEQ ID NO 40
<211> LENGTH: 118
<212> TYPE: DNA
<213> ORGANISM: human rhinovirus

<400> SEQUENCE: 40
gagaagcctt attattgaca aggtgtgaag agccgcgtgt gcttggtgtg agtcctccgg      60
cccctgaatg tggctaacct taaccctgca gccattgctc ataatccaat gagttagt      118

<210> SEQ ID NO 41
<211> LENGTH: 117
<212> TYPE: DNA
<213> ORGANISM: human rhinovirus

<400> SEQUENCE: 41
aggacgctag tagtgaacaa ggtgtgaaga gcccactgag ctacctgaga atcctccggc      60
ccctgaatgc ggctaatccc aaccacggag caggtaatcg caaaccagcg gtcagcc        117

<210> SEQ ID NO 42
<211> LENGTH: 119
<212> TYPE: DNA
<213> ORGANISM: human rhinovirus

<400> SEQUENCE: 42
gggacgccct tttaaggaca tggtgtgaag actcgcatgt gcttggttgt gagtcctccg      60 gccccctgaat gcggctaacc ttaaccctag agccttatgc cacgatccag tggttgtaa    119

<210> SEQ ID NO 43
<211> LENGTH: 118
<212> TYPE: DNA
<213> ORGANISM: human rhinovirus

<400> SEQUENCE: 43
gtgaagccaa gtattggaca aggtgtgaag agccgcgtgt gctcatcttg agtcctccgg    60
cccctgaatg tggctaacct taaacctgca gccagtgcac acaatccagt gtgtagct    118

<210> SEQ ID NO 44
<211> LENGTH: 119
<212> TYPE: DNA
<213> ORGANISM: human rhinovirus

<400> SEQUENCE: 44
gggacgcctt aattgtgaca tggtgtgaag acccacgtgt gcttaattgt gagtcctccg    60 gccccctgaat gcggctaacc taaaccctgg agccttgaga cacaatccag tgttggcaa    119

<210> SEQ ID NO 45
<211> LENGTH: 118
<212> TYPE: DNA
<213> ORGANISM: human rhinovirus

<400> SEQUENCE: 45
gcgaagccat acattggaca aggtgtgaag agcccgtgt gctcactttg agtcctccgg     60
cccctgaatg tggctaacct taaccctgca gctagtgcat gtaatccaac atgttgct    118

<210> SEQ ID NO 46
<211> LENGTH: 118
<212> TYPE: DNA
<213> ORGANISM: human rhinovirus

<400> SEQUENCE: 46
gtgaagccat atttttgaca aggtgtgaag agcccgtgt gctcattttg agtcctccgg     60
cccctgaatg tggctaacct taaccctgca gctagtgcat gcaatccagc atgttgct    118

<210> SEQ ID NO 47
<211> LENGTH: 119
<212> TYPE: DNA
<213> ORGANISM: human rhinovirus

<400> SEQUENCE: 47
gggacgcctt tttatggaca tggtgtgaag actcgcatgt gcttggttgt gactcctccg    60 gccccctgaat gcggctaacc ttaaccccgg agccctgtgt tgcaatccag taacattag    119

<210> SEQ ID NO 48
<211> LENGTH: 118
<212> TYPE: DNA
<213> ORGANISM: human rhinovirus
<220> FEATURE:
<221> NAME/KEY: misc_feature
<222> LOCATION: 78, 89, 92, 110
<223> OTHER INFORMATION: n = A,T,C or G

<400> SEQUENCE: 48
gtgaagccat tcattggaca gggtgagaag agcccagtgt gctcattttg agtcctccgg    60
cccctgaatg tggctaanct taaacctgna gncaatgcac acaatccagn gtgtattt    118

<210> SEQ ID NO 49
<211> LENGTH: 117
<212> TYPE: DNA
<213> ORGANISM: human rhinovirus

<400> SEQUENCE: 49
aggacgctag tagtgaacaa ggtgtgaaga gcccactgag ctacctgaga atcctccggc    60

```
ccctgaatgc ggctaatccc aaccacggag caggtaatcg caaaccagcg gtcagcc      117
```

<210> SEQ ID NO 50
<211> LENGTH: 118
<212> TYPE: DNA
<213> ORGANISM: human rhinovirus

<400> SEQUENCE: 50

```
gcgaagccaa gtaacggaca gggtgtgaag agccccgtgt gctcgatttg agtccttcgg   60
ccctgaatg tggctaacct taaccctgca gctagggcac acaatccagt gtgtatct     118
```

<210> SEQ ID NO 51
<211> LENGTH: 119
<212> TYPE: DNA
<213> ORGANISM: human rhinovirus

<400> SEQUENCE: 51

```
gggacgcctt aagtatgaca tggtgtgaag acccgcatgt gcttaactgt gagtcctccg   60
gccctgaat gcggctaacc ttaaccctgg agccttggag tacaatccag tgctaacaa    119
```

<210> SEQ ID NO 52
<211> LENGTH: 118
<212> TYPE: DNA
<213> ORGANISM: human rhinovirus

<400> SEQUENCE: 52

```
gtgaagccat atatttgaca aggtgtgaag agccccgtgt gctcactttg agtcctccgg   60
ccctgaatg tggctaacct taaccctgca gctagtgtat gtaatccaac atatggct     118
```

<210> SEQ ID NO 53
<211> LENGTH: 120
<212> TYPE: DNA
<213> ORGANISM: human rhinovirus

<400> SEQUENCE: 53

```
gggacgcccc gattgcgaca cggggtgaag acccgcgtgt gctcaactgt gagacctccg   60
gccctgaat gcggctaacc taaaccctgg agcctcgaaa cacaacccag atgttcgcaa   120
```

<210> SEQ ID NO 54
<211> LENGTH: 119
<212> TYPE: DNA
<213> ORGANISM: human rhinovirus

<400> SEQUENCE: 54

```
gggacgcctt aattgtgaca tggtgcgaag acccacgtgt gcttaattgt gagtcctccg   60
gccccgaat gcggctaacc taaaccccgg agccttgaga cacaatccag tgttagcaa    119
```

<210> SEQ ID NO 55
<211> LENGTH: 119
<212> TYPE: DNA
<213> ORGANISM: human rhinovirus

<400> SEQUENCE: 55

```
gggacgccct ttcaatgaca tggtgtgaag actcgcatgt gcttgattgt gagtccgccg   60
gccctgaat gcggctaacc ctaaccctgg agccttgcac cacaatccag tggtgtctg    119
```

<210> SEQ ID NO 56
<211> LENGTH: 119
<212> TYPE: DNA
<213> ORGANISM: human rhinovirus

```
<400> SEQUENCE: 56 gggacgccctt tcaagagaca tggtgtgaag actcaattgt gcttggttgt gagtcctccg    60 gccectgaat gcggctaacc ttaaacccgg atccatgcta tgcaaaccag catagttat    119

<210> SEQ ID NO 57
<211> LENGTH: 118
<212> TYPE: DNA
<213> ORGANISM: human rhinovirus
<220> FEATURE:
<221> NAME/KEY: misc_feature
<222> LOCATION: 92
<223> OTHER INFORMATION: n = A,T,C or G

<400> SEQUENCE: 57
gtgaagccat acatttgaca aggtgtgaag agccccgtgt gctcactttg agtcctccgg    60 ccectgaatg tggctaacct taaccctgca gntggtgcat gtaatccaac atgttgct    118

<210> SEQ ID NO 58
<211> LENGTH: 119
<212> TYPE: DNA
<213> ORGANISM: human rhinovirus

<400> SEQUENCE: 58
gggacgccaa tttgttgaca tggtgtgaag atcttaatgt gcttggttgt gagtcctccg    60 gccectgaat gcggctaacc ttaaccccgg agccttgtgt cacaagccag tgacattaa    119

<210> SEQ ID NO 59
<211> LENGTH: 117
<212> TYPE: DNA
<213> ORGANISM: human rhinovirus

<400> SEQUENCE: 59
gagacgctag acatgaacaa ggtgtgaaga gtttattgag ctactataga gtcctccggc    60
ccctgaatgc ggctaatcct aaccatggag caagtgctca caaaccagtg ggttgct     117

<210> SEQ ID NO 60
<211> LENGTH: 119
<212> TYPE: DNA
<213> ORGANISM: human rhinovirus

<400> SEQUENCE: 60 gggacgccctt aattgtgaca tggtgtgaag acccacgtgt gcttaattgt gagtcctccg    60 gccectgaat gcggctaacc taaaccctgg agccttgaaa cacaatccag tgttagcaa    119

<210> SEQ ID NO 61
<211> LENGTH: 117
<212> TYPE: DNA
<213> ORGANISM: enterovirus

<400> SEQUENCE: 61
aggacgctag ttgtgaacaa ggtgtgaaga gcctattgag ctacctgaga gtcctccggc    60
ccctgaatgc ggctaatcct aaccacggag caggcagtgg caatccagcg accagcc     117

<210> SEQ ID NO 62
<211> LENGTH: 118
<212> TYPE: DNA
<213> ORGANISM: enterovirus

<400> SEQUENCE: 62
aggacgctct aatatggaca tggtgtgaag agtctattga gctagttagt agtcctccgg    60
```

```
cccctgaatg cggctaatcc taactgcgga gcacgtacct ccaatccagg aggtggcg      118
```

<210> SEQ ID NO 63
<211> LENGTH: 118
<212> TYPE: DNA
<213> ORGANISM: enterovirus

<400> SEQUENCE: 63

```
aggacgctct aatgctgaca tggtgcgaag agtctattga gctagctggt agtcctccgg      60
cccctgaatg cggctaatcc caactgcgga gcacgcaccc tcaaaccagg gggcagcg      118
```

<210> SEQ ID NO 64
<211> LENGTH: 118
<212> TYPE: DNA
<213> ORGANISM: enterovirus

<400> SEQUENCE: 64

```
aggacgctct aatatggaca tggtgcaaag agtctattga gctagttagt agtcctccgg      60
cccctgaatg cggctaatcc taactgcgga gcacataccc tcgacccagg gggcagtg      118
```

<210> SEQ ID NO 65
<211> LENGTH: 117
<212> TYPE: DNA
<213> ORGANISM: enterovirus

<400> SEQUENCE: 65

```
gggacgctag ttgtgaacaa ggtgtgaaga gcctattgag ctactcaaga gtcctccggc      60
ccctgaatgc ggctaatcct aaccacggag caatcgctca cgacccagtg agtaggt         117
```

<210> SEQ ID NO 66
<211> LENGTH: 118
<212> TYPE: DNA
<213> ORGANISM: enterovirus

<400> SEQUENCE: 66

```
gggacgcttc aatactgaca cggtgtgaag agtctattga gctaattggt agtcctccgg      60
cccctgaatg cggctaatcc taactgcgga gcagataccc acgcgccagt gggcagtc      118
```

<210> SEQ ID NO 67
<211> LENGTH: 118
<212> TYPE: DNA
<213> ORGANISM: enterovirus

<400> SEQUENCE: 67

```
gggacgctct aatacagaca tggtgcgaag agtctattga gctagttggt agtcctccgg      60
cccctgaatg cggctaatcc taactgcgga gcacacaccc tcaagccaga gggcagtg      118
```

<210> SEQ ID NO 68
<211> LENGTH: 118
<212> TYPE: DNA
<213> ORGANISM: enterovirus

<400> SEQUENCE: 68

```
gggacgcttc aatactgaca tggtgcgaag agtcaattga gctagttggt agtcctccgg      60
cccctgaatg cggctaatcc taactgtgga gcagataccc acagaccagt gggcagtc      118
```

<210> SEQ ID NO 69
<211> LENGTH: 118
<212> TYPE: DNA
<213> ORGANISM: enterovirus -continued

```
<400> SEQUENCE: 69
aggacgctct aatgtggaca tggtgcgaag agcctattga gctagttagt agtcctccgg      60
cccctgaatg cggctaatcc taactgcgga gcacatgcct tcaacccaga gggtagtg       118

<210> SEQ ID NO 70
<211> LENGTH: 118
<212> TYPE: DNA
<213> ORGANISM: enterovirus

<400> SEQUENCE: 70
aggacgctct aatatggaca tggtgcaaag agtctattga gctagttagt agtcctccgg      60
cccctgaatg cggctaatcc taactgcgga gcacataccc tcgacccagg gggcagtg       118

<210> SEQ ID NO 71
<211> LENGTH: 118
<212> TYPE: DNA
<213> ORGANISM: enterovirus

<400> SEQUENCE: 71
aggacgctct aatacagaca tggtgcgaag agtctattga gctagttggt aatcctccgg      60
cccctgaatg cggctaatcc taactgcgga gcatataccc tcaaaccagg gggcagtg       118

<210> SEQ ID NO 72
<211> LENGTH: 22
<212> TYPE: DNA
<213> ORGANISM: Artificial Sequence
<220> FEATURE:
<223> OTHER INFORMATION: primer

<400> SEQUENCE: 72
ggtgtgaaga sycvcrtgtg ct                                              22

<210> SEQ ID NO 73
<211> LENGTH: 22
<212> TYPE: DNA
<213> ORGANISM: Artificial Sequence
<220> FEATURE:
<223> OTHER INFORMATION: probe

<400> SEQUENCE: 73
tgagtcctcc ggcccctgaa tg                                              22

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
ggctaacctw aamccyrsag c                                               21
```